US010724106B2

(12) United States Patent
Antikainen et al.

(10) Patent No.: US 10,724,106 B2
(45) Date of Patent: Jul. 28, 2020

(54) METHOD FOR DETERMINING THE PRESENCE OF DIARRHOEA CAUSING PATHOGENS

(71) Applicant: MOBIDIAG OY, Espoo (FI)

(72) Inventors: Jenni Antikainen, Espoo (FI); Juha Kirveskari, Espoo (FI)

(73) Assignee: MOBIDIAG OY, Espoo (FI)

( * ) Notice: Subject to any disclaimer, the term of this patent is extended or adjusted under 35 U.S.C. 154(b) by 767 days.

(21) Appl. No.: 14/411,170

(22) PCT Filed: Jun. 27, 2013

(86) PCT No.: PCT/FI2013/050716
§ 371 (c)(1),
(2) Date: Dec. 24, 2014

(87) PCT Pub. No.: WO2014/001648
PCT Pub. Date: Jan. 3, 2014

(65) Prior Publication Data
US 2015/0299774 A1     Oct. 22, 2015

Related U.S. Application Data

(60) Provisional application No. 61/664,959, filed on Jun. 27, 2012.

(30) Foreign Application Priority Data

Jun. 27, 2012 (FI) ...................... 20125730

(51) Int. Cl.
| C12Q 1/689 | (2018.01) |
| C12Q 1/6888 | (2018.01) |
| C12Q 1/6893 | (2018.01) |
| G01N 33/50 | (2006.01) |

(52) U.S. Cl.
CPC .......... *C12Q 1/689* (2013.01); *C12Q 1/6888* (2013.01); *C12Q 1/6893* (2013.01); *C12Q 2600/16* (2013.01); *Y02A 50/52* (2018.01)

(58) Field of Classification Search
CPC .... C12Q 1/6888; C12Q 1/689; C12Q 1/6893; C12Q 2600/16
See application file for complete search history.

(56) References Cited

U.S. PATENT DOCUMENTS

| 2004/0248148 A1 | 12/2004 | Horgen Et El |
| 2013/0059756 A1 | 3/2013 | Yamasaki et al. |

FOREIGN PATENT DOCUMENTS

| CN | 101113471 A | 1/2008 |
| CN | 101235410 A | 8/2008 |
| CN | 101245384 A | 8/2008 |
| CN | 101760517 A | 6/2010 |
| CN | 101831491 A | 9/2010 |
| CN | 101113475 B | 10/2010 |
| EP | 0 266 244 A2 | 4/1988 |
| EP | 242334 A1 | 2/2012 |
| WO | WO 02/070728 A2 | 9/2002 |
| WO | WO 2005/005659 A1 | 1/2005 |
| WO | WO 2005/083122 A2 | 9/2005 |
| WO | WO 2005/090596 A2 | 9/2005 |
| WO | WO 2007/056463 A2 | 5/2007 |
| WO | WO 2010/123058 A1 | 10/2010 |
| WO | WO 2011/044499 A2 | 4/2011 |
| WO | WO 2011/129091 A1 | 10/2011 |

OTHER PUBLICATIONS

Aranda, K.R.S. et al., FEMS Microbiol. Lett., vol. 267, pp. 145-150, (2007).*
Fukushima, F. et al., Comprehensive and Rapid Real-Time PCR Analysis of 21 Foodborne Outbreaks, Int. J. Microbiol., vol. 2009, ID 917623, pp. 1-13 (Year: 2009).*
GenBank Accession No. M25607, *E. coli* heat stable enterotoxin I gene, complete cds (Year: 1993).*
GenBank Accession No. M29255, *E. coli* heat-stable toxin (st) gene, complete Cds (Year: 1993).*
GenBank Accession No. M34916, *E. coli* heat-stable enterotoxin gene, complete cds (Year: 1993).*
GenBank Aceession No. EU113244, *Escherichia coli* strain 121-I elt operon, complete sequence (Year: 2008).*
Antikainen, J. et al., New 16-plex PCR method for rapid detection of diarrheagenic *Escherichia coli* directly from stool samples, Eur. J. Clin. Microbiol. Infect. Dis., vol. 28, pp. 899-908 (Year: 2009).*
Antikainen et al., "A Quantitative Polymerase Chain Reaction Assay for Rapid Detection of 9 Pathogens Directly from Stools of Travelers with Diarrhea," Clinical Gastoenterology and Hepatology (2013) vol. 11, pp. 1300-1307.
Fujioka et al., "Direct detection of diarrheagenic *Escherichia coli* in patient stool speimens by developed Multiplex PCRs,"Igaku Kensa (2008), vol. 57, pp. 1041-1046.
Fukushima et al., "Duplex Real-Time SYBR Green PCR Assays for Detection of 17 Species of Food- or Waterborne Pathogens in Stools," Journal of Clinical Microbiology (Nov. 2003), vol. 41, No. 11, pp. 5134-5146.
Hidaka et al., "Multiplex real-time PCR for exhaustive detection of diarrhoeagenic *Escherichi coli*," Journal of Applied Microbiology (2009), vol. 106, pp. 410-420.

(Continued)

*Primary Examiner* — Teresa E Strzelecka
(74) *Attorney, Agent, or Firm* — Birch, Stewart, Kolasch & Birch, LLP

(57) ABSTRACT

This invention relates to the field of detection of diarrhoea causing pathogens from patient, food or environmental samples. Particularly, the present invention provides a polymerase chain reaction (PCR) based assay method for detection of diarrhoea causing pathogens. The present invention further provides materials such as primers, primer pairs and probes for use in the method of the invention. Preferably, the method of the invention is a multiplex real-time PCR (RT-PCR) assay for rapid determination of clinically important pathogens related to traveller's diarrhoea.

19 Claims, No Drawings

Specification includes a Sequence Listing.

(56) References Cited

OTHER PUBLICATIONS

International Preliminary Report on Patentability and Written Opinion dated Jan. 8, 2015, in PCT International Application No. PCT/FI2013/050716.

International Search Report dated Nov. 25, 2013, in PCT International Application No. PCT/FI2013/050716.

Kodama et al., "Study on Real-Time PCR Assays for Simultaneous Detection of Food-Borne Pathogens," Hokuriku Koshu Eisei Gakkaishi (2008), vol. 34, pp. 65-72.

Lothigius, "Enterotoxigenic *Escherichia coil* is detectable in water samples form an endemic area by real-time PCT," Journal of Applied Microbiology (2008), vol. 104, pp. 1128-1136.

Reischl et al., "Real-Time Fluorescence PCR Assays for Detection and Characterization of Heat-Labile I and Heat Stable I Enterotoxin Genes from *Escherichia Coli*," Journal of Clinical Microbiology (Sep. 2004), vol. 42, No. 9, pp. 4092-4100.

Search Report dated Apr. 18, 2013, in Finnish Patent Application No. 20125730.

Wang et al., "Development of a DNA Microarray for Detection and Serotyping of Enterotoxigenic *Escherichia Coli*," Journal of Clinical Microbiology (Jun. 2010), vol. 48, No.6, pp. 2066-2074.

West et al., "Rapid detection of *Escherichia coli* virulence factor genes using multiplex real-time TaqMan(R) PCR assays," Veterinary Microbiology (2007), vol. 122, pp. 323-331.

Zhang et al., "Taqman triplex real-time PCR assays for rapid detection of diarrhea-genic *Escherichia coli* in raw milk," Journal of Northeast Agricultural University (Oct. 2010), vol. 41, No. 10, pp. 108-115.

Kimata et al., "Rapid Categorization of Pathogenic *Escherichia coli* by Multiplex PCR," Microbiol. Immunol., vol. 49, No. 6, 2005, pp. 485-492.

* cited by examiner

METHOD FOR DETERMINING THE PRESENCE OF DIARRHOEA CAUSING PATHOGENS

CROSS REFERENCE TO RELATED APPLICATIONS

This application is the National Phase of PCT/FI2013/050716 filed on Jun. 27, 2013, which claims priority under 35 U.S.C. 119(e) to U.S. Provisional Application No. 61/664,959 filed on Jun. 27, 2012 and under 35 U.S.C. 119(a) to Patent Application No. 20125730 filed in Finland on Jun. 27, 2012, all of which are hereby expressly incorporated by reference into the present application.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-06-08-SEQLIST-TEXT-0933-0640PUS2.txt" created on Jun. 8, 2015 and is 16,567 bytes in size. The sequence listing contained in this .txt file is part of the specification and is hereby incorporated by reference herein in its entirety.

FIELD OF THE INVENTION

This invention relates to the field of detection of diarrhoea causing pathogens from patient, food or environmental samples. Particularly, the present invention provides a polymerase chain reaction (PCR) based assay method for detection of diarrhoea causing pathogens, particularly ETEC and *Campylobacter* species. The present invention further provides materials such as primers, primer pairs and probes for use in the method of the invention. Preferably, the method of the invention is a multiplex real-time PCR (RT-PCR) assay for rapid determination of clinically important pathogens related to traveller's diarrhoea.

BACKGROUND OF THE INVENTION

Diarrhoea is a major health problem worldwide causing morbidity, but also mortality especially of infants in the developing countries. Diarrhoea is the most reported problem for travellers and is commonly caused by contamination of food or water. In most cases traveller's diarrhoea is mild and short of duration, but severe infections with abdominal pain, bloody diarrhoea and septicaemia exist.

The causes of acute diarrhoea of travellers are many and varied. In addition to classical diarrhoeal bacteria, such as *Salmonella, Campylobacter, Shigella* and *Yersinia* also diarrhoeal *E. coli* strains are associated with traveller's diarrhoea. (enterohemorrgenic *E. coli*; EHEC, enterotoxigenic *E. coli*; ETEC, attaching and effacing *E. coli*; A/EEC or enteroaggregative *E. coli*; EAEC, enteropathogenic *E. coli*; EPEC, verocytotoxin producing *E. coli*; VTEC, enterohemorrhagic *E. coli*; EHEC, enteroinvasive *E. coli*; EIEC). *Salmonella* infection can cause a variable clinical disease starting from a mild, subclinical infection, or lead to severe systemic infection, typhoid fever. *Salmonella* sp. invades the host through the colonic epithelial cells, especially M cells using a type III secretion system. They are also able to survive within phagosomes of macrophages, and evade the host immune system by several ways (Coburn et al., 2007). *Campylobacter jejuni* and *coli* are among the large *Campylobacter* family predominant human stool pathogens causing watery diarrhoea, fever and typically hard abdominal pain. By diagnostic means they must be dissected from the other *Campylobacter* species not associated with diarrhoea. They are able to invade the colonic epithelium lining and replicate intracellularly and cause apoptosis (Poly and Guerry, 2008; Allos, 2001). *Yersinia enterocolitica* and *pseudotuberculosis* harbour a virulence plasmid containing relevant adhesion and invasion proteins, such as YadA (Bottone, 1999, El Tahir et al., 2001). For *Y. enterocolitica* a virulence plasmid is required to cause a clinical disease, whereas *Y. pseudotuberculosis* has additional genomic virulence factors as well. *Yersinia pestis* is the plague pathogen, which harbours genomic virulence factors and three virulence plasmids which are all required to cause a clinical disease (Bottone, 1999). The traditional pathogens are also associated with late onset symptoms, such as reactive arthritis, sacroiliitis and acute anterior uveitis.

*Vibrio cholerae* is a highly virulent environmental pathogen living in free waters in some of the tropical countries, especially causing epidemics in catastrophe areas. It typically causes massive watery diarrhoea leading to patient death if not sufficiently resuscitated. The essential virulence factor is cholera toxin which consists of two subunits A and B. The cholera toxin is able to bind irreversibly to the G-proteins in the colonic epithelial cells responsible for liquid and electrolyte uptake causing non-voluntary continuous secretion into gut lumen (Nelson et al., 2009).

*Shigella* and EIEC are genetically closely related. Both of these organisms invade the colonic epithelium mediated by the genes located in virulence plasmid pINV coding e.g. Ipa proteins and their transcription regulator invE (Lan and Reeves, 2002; Parsot, 2005). EAEC demonstrate characteristic adherence pattern to Hep-2 cells via specific fimbria encoded by genes which are located on plasmid under the regulation of AggR (Flores and Okhuysen, 2009). EPEC is characterized to possess pathogenicity island named the locus of enterocyte effacement (LEE). This island contains genes such as eae for intimate adherence of the EPEC strains to intestinal epithelial cells. EPEC is differentiated from EHEC by ability of EHEC strains to production shiga-like toxins I and II encoded by stx1 and stx2 genes. These cytotoxins cause acute inflammation in the intestine leading to abdominal pain and bloody diarrhoea. In addition, EHEC infection may lead to rare but severe, secondary complications such as haemolytic uremic syndrome (HUS) (Chen and Frankel, 2005; Karch et al., 2005). The challenge in multiplex PCR assays is to identify EHEC variants so that there is no cross-reaction with *Shigella*/EIEC species, because the target genes expressing toxins in these bacteria are very similar.

Giardiasis is an infection of the small intestine caused by *Giardia lamblia* (also known as *G. intestinalis*), a flagellate protozoan. Giardiasis is the most commonly reported pathogenic protozoan disease worldwide. Travelers are the largest risk group for giardiasis infection, especially those who travel to the developing world. Giardiasis is spread via the fecal-oral route. Most people contract the disease by ingesting contaminated water or food, or by not washing their hands after touching something contaminated with *Giardia* cysts. Prevalence rates for giardiasis range from 2-7% in developed countries and 20-30% in most developing countries. The CDC estimates there are an upwards of 2.5 million cases of giardiasis annually. The most common symptoms of *Giardia* infection include diarrhea for a duration of more than 10 days, abdominal pain, flatulence, bloating, vomiting, and weight loss. Giardiasis is traditionally diagnosed by the detection of cysts or trophozoites in the feces, trophozoites in the small intestine, or by the detection of *Giardia* antigens in the feces.

Currently, the routine diagnostic of diarrhoea is mostly based on traditional cultivation methods and immunoassays, which are both laborious and time consuming. They are only available for *Salmonella, Campylobacter, Shigella* and *Yersinia* species as well as enterohaemorrhagic *Escherichia coli* (EHEC), whereas no cultivation method for other major diarrhoeagenic *E. coli* species, including ETEC, EPEC, EAEC, and EIEC exists. In recent years, DNA based methods for diagnosis of diarrhoeagenic *E. coli* has been published (Antikainen et al., 2009; Aranda et al., 2004; Brandal et al., 2007; Guion et al., 2008; Kimata et al., 2005; Müller et al., 2007; Vidal et al., 2005; Vidal et al., 2004).

ETEC causes watery diarrhoea by producing heat-labile (LT) and/or heat-stable (ST) enterotoxins [2-3]. ETEC is traditionally considered the most common cause in traveller's diarrhoea (Qadri et al., 2005). The present invention is particularly directed to improve the detection of ETEC in multiplex RT-PCR assays. The present invention provides two primer pairs and probes specific for the heat stable enterotoxin of ETEC encoded by the est gene and one primer pair and probe specific for the heat labile enterotoxin of ETEC encoded by the elt gene. These primers and probes are designed to amplify such target sequences in said genes that it renders possible efficient detection of global variants of ETEC. Further problem was that the target gene est includes multiple repetitive elements and it was difficult to find conserved regions long enough for both the primers and the probe.

The present invention is further directed to improve the detection of diarrhea causing *Campylobacter* species in multiplex RT-PCR assays. The invention provides primer pairs and probes for rimM gene of *C. jejuni* and gyrB gene of *C. coli*. With these primers and probes the diarrhoea causing *Campylobacter* can be distinctively identified from other non-pathogenic *Campylobacter* and other diarrhea causing pathogens. A combination of two different genomic targets was required to solve the problem.

In WO2005/005659, it is disclosed a method for simultaneous screening diarrhoea causing bacteria such as *E. coli* groups: ETEC (enterotoxigenic *E. coli*), A/EEC (attaching and effacing *E. coli*) EPEC (enteropathogenic *E. coli*), VTEC (verocytotoxin producing *E. coli*) and EIEC (enteroinvasive *E. coli*); and *Shigella* spp. The method is a real-time multiplex PCR assay and the template DNA is isolated directly from a stool sample. Similarly as the present invention, WO2005/005659 is also directed to the problem of screening for human pathogenic *E. coli* in order to provide distinction between the pathogenic *E. coli* groups and other diarrhoea causing pathogens. However, the target sequences in est and elt genes of ETEC are different in the present invention from the targets disclosed by WO2005/005659. Moreover, the present invention is providing coverage of global ETEC variants by the use of three specific primer pairs and probes while WO2005/005659 in Table 3 discloses four primer pairs for the same purpose. Table 8 of the present specification show that ETEC variants can be detected by using the three primer pairs of the present invention.

In WO2005/083122, it is disclosed a method for detection and quantification of enteropathogenic bacteria in a fecal specimen, including *Shigella* species, *Salmonella* species, *Campylobacter* species, enterohemorrhagic *Escherichia coli* or Verocytotoxin-producing *Escherichia coli*, *Vibrio cholerae*, and *Clostridium perfringens*. The method is a real-time PCR assay based on TaqMan® probes.

In WO2007/056463, it is disclosed a method comprising amplification of a sample with a plurality of pathogen-specific primer pairs to generate amplicons of distinct sizes from each of the pathogen specific primer pairs. The method utilizes real-time and multiplex PCR techniques. The method can be used for the detection of *Salmonella* species, *Campylobacter* species, diarrhoeagenic *Escherichia coli*, *Vibrio cholerae*, *Yersinia* species such as *Yersinia pestis*, and *Giardia lamblia*.

In WO2005/090596, it is disclosed an assay for detecting micro-organisms, and in particular bacteria, based on multigenotypic testing of bacterial DNA from human, animal or environmental samples. The method may also be utilized as a real-time multiplex PCR technique using TaqMan® probes. The method can be used for the detection of *Salmonella* species, *Campylobacter* species, diarrhoeagenic *Escherichia coli*, *Vibrio cholerae*, *Yersinia* species such as *Yersinia pestis*.

In US2004/0248148, it is disclosed a 5' nuclease real-time polymerase chain reaction approach for the quantification of total coliforms, *E. coli*, toxigenic *E. coli* O157:H7, toxigenic *M. aeruginosa* (microcystin hepatotoxins), *Giardia lamblia*, and *Cryptosporidium parvum*. Multiplex PCR assay can also be used for simultaneous detection of two or more pathogens.

In WO02/070728, it is disclosed an assay that relies on a 'multiprobe' design in which a single set of highly conserved sequences encoded by the 16S rRNA gene serves as the primer pair, and it is used in combination with both an internal highly conserved sequence, the universal probe, and an internal variable region, the species-specific probe. The real-time system reliably identifies 14 common bacterial species.

CN101113471, CN101245384 and CN101235410 disclose PCR methods for rapid detection of diarrhoea causing pathogens from food samples.

Fukushima et al., 2003, disclose a real-time PCR assay for detection of 17 species of food- or waterborne pathogens directly from stool sample. The detection levels were approximately $10^5$ pathogenic bacteria per gram of stool, therefore the protocol for stool specimens for less than $10^4$ pathogenic bacteria per gram of stool requires an overnight enrichment step to achieve adequate sensitivity.

Hidaka et al., 2009, disclose multiplex real-time PCR for exhaustive detection of diarrhoeagenic *E. coli*. This method is especially for the detection of pathogenic bacteria from a food sample, such as meat sample.

Wang et al., 1997, disclose a protocol for PCR detection of 13 species of foodborne pathogens in foods.

There are some commercial multiplex PCR-based diarrheal pathogen detection kits available, for example xTAP GPP from Luminex and Diarrhea ACE Detection from Seegene. Both systems use multiplex PCR as a means for amplifying certain organism-specific nucleotide sequences but the final detection relies on analysis in another separate instrument. The means used for detection has an impact on the amplicon, primer and probe design because of different requirements of the detection formats. Further, gene or amplicon sequences used in the present invention for the detection of ETEC or *Campylobacter* have not been disclosed.

The number of pathogens causing diarrhoea is large and a diarrhoea test method should optimally identify all of them. Having one PCR reaction per species can be cumbersome, since the number of samples tested is typically large. It would be optimal to detect multiple species within one reaction. In a PCR setting the most obvious alternative is 'multiplex' PCR amplification. In multiplex PCR, several oligonucleotide sets, each designed to amplify one species/species group, are included in the same reaction vessel and each oligonucleotide set is used to amplify its respective pathogen DNA during the same PCR reaction. In this invention, we describe a PCR based method for rapid detection of clinically important pathogens related to traveller's diarrhea, particularly ETEC and/or *Campylobacter*. The present invention discloses primers and probes designed for target sequences conserved in global variants of ETEC and *Campylobacter*. These primers and probes are compatible for use in any multiplex RT-PCR determining the presence of multiple diarrhoea causing pathogens, since the target sites are unique for ETEC and *Campylobacter*.

Multiplex PCR presents a challenge for quantitation of the pathogen DNA (qPCR): the different amplicons compete for the same PCR reaction components (eg. DNA polymerase and MgCl2) and this can compromise the quantitative nature of the reaction between and, especially, quantitative comparisons between samples. It is commonly known in the art that there is bias in the amplification efficiencies between different template amounts or lengths so that e.g. short amplicons are favoured in the expense of longer ones.

At the same time, undesired cross-reactions of multiplex set oligo combinations must be avoided. One must also remember to check mis-priming to any other sequences present in the sample.

Finding suitable primer and probe sequences for the detection of a diverse group of pathogenic microbes can be far from trivial especially when designing multiplex set ups where all amplicons and templates should be amplified with equal efficiency (e.g., *Giardia*). Many of the species are relatively closely related, making it challenging to locate sequences that are unique for each species. Also, as there are a significant number of global variants, it is difficult to identify globally conserved regions or a combination of minimal set of regions to detect all known variants (e.g., for EHEC, ETEC, pathogenic *Yersinia*, pathogenic *Campylobacter* and *Shigella*/EIEC). Some genes possess complex repetive closely related elements which is challenging from the amplicon design point of view, especially when designing amplicons for multiplex PCR. For example, due to repetitive elements and minor variants ETEC cannot be detected using only one amplicon.

The sample matrix, which in diarrhoea diagnostics is commonly a stool or food sample, is likely to contain a host of PCR inhibitors. This reduces amplification efficiency of the PCR reaction and thus even more careful optimization is expected from the amplicon design step to verify that all templates and copy numbers are amplified equally but also efficiently enough. Hence, oligonucleotide design enabling high PCR efficiency (optimally as close to 100% as possible) is required. The detection method used may also affect amplification efficiency and/or bias.

The present inventors have now located DNA sequence regions that are well suited for specific and sensitive amplification and quantification of diarrhoea causing pathogens, particularly ETEC and *Campylobacter*. Accordingly, optimal primers and quantitative PCR probes have been designed in the present invention and validated for identification and quantification of diarrhoea causing pathogens. The amplicons have been designed to be so specific that they can be combined into any multiplex sets with each other. Naturally a prerequisite to this is that all the disclosed amplicons have also been designed to amplify in the same reaction and cycling conditions.

DETAILED DESCRIPTION OF THE INVENTION

The present invention provides a polymerase chain reaction (PCR) based assay method for detection of diarrhoea causing pathogens, particularly ETEC and *Campylobacter* species. The present invention further provides materials such as primers, primer pairs and probes for use in the method of the invention. Particularly, the present invention provides a method for determining the presence of diarrhoea causing pathogens in a biological sample comprising the steps of: i) contacting the sample or nucleic acid isolated therefrom with primer pairs in a multiplex PCR assay comprising two or more separate PCR reactions, wherein the primers of said primer pairs amplify any of the amplicons as defined by SEQ ID NOS:55-72, preferably SEQ ID NOS: 61-63 and 65-68, at least partly;
ii) performing a polymerase chain reaction with reaction mixes obtained from step i) so that the target sequences of diarrhoea causing pathogens are specifically amplified, if said sequences are present in the sample; and
iii) detecting the presence of amplified target sequences in the reaction mix, wherein the presence of any of the target sequences is indicative of the presence of diarrhoea causing pathogens in the sample.

Said biological sample can be a stool sample, a food sample, such as a meat sample, or any environmental sample. The sample may be enriched before step i).

Preferably, the primer pairs in step i) of the method are selected from the group consisting of primer pairs A) to R), more preferably G) to I) and K) to N), comprising or consisting of at least one of the following oligonucleotides:

```
A) forward primer:
                            (SEQ ID NO: 1)
5'GCGTTCTTATGTAATGACTGCTGAAG-3', reverse primer:
                            (SEQ ID NO: 2)
5'-AGAAATTCTTCCTACACGAACAGAGTC-3';

B) forward primer:
                            (SEQ ID NO: 3)
5'-TGCATCCAGAGCAGTTCTGC-3', reverse primer:
                            (SEQ ID NO: 4)
5'-CGGCGTCATCGTATACACAGG-3';

C) forward primer:
                            (SEQ ID NO: 5)
5'-CCAGGCTTCGTCACAGTTGC-3', reverse primer:
                            (SEQ ID NO: 6)
5'-CAGTGAACTACCGTCAAAGTTATTACC-3';

D) forward primer:
                            (SEQ ID NO: 7)
5'-GCTCTTCGGCACAAGTAATATCAAC-3', reverse primer:
                            (SEQ ID NO: 8)
5'-TCTATTTTAAATTCCGTGAAGCAAAACG-3';

E) forward primer:
                            (SEQ ID NO: 9)
5'-TGGTCCATCAGGCATCAGAAGG-3',
```

-continued
reverse primer:
(SEQ ID NO: 10)
5'-GGCAGTGCGGAGGTCATTTG-3';

F) forward primer:
(SEQ ID NO: 11)
5'-TGTCTTTATAGGACATCCCTGATACTTTC-3', reverse primer:
(SEQ ID NO: 12)
5'-TATCTACTCTTGATGCCAGAAAACTAGC-3';

G) forward primer:
(SEQ ID NO: 13)
5'-AAAATTGCAAAATCCGTTTAACTAATC-3', reverse primer:
(SEQ ID NO: 14)
5'-GACTGACTAAAAGAGGGGAAAG-3';

H) forward primer:
(SEQ ID NO: 15)
5'-TCCTGAAAGCATGAATAGTAGC-3', reverse primer:
(SEQ ID NO: 16)
5'-TTATTAATAGCACCCGGTACAAG-3';

I) forward primer:
(SEQ ID NO: 17)
5'-CCGGCAGAGGATGGTTACAG-3', reverse primer:
(SEQ ID NO: 18)
5'-TTGATTGATATTCCCTGAGATATATTGTG-3';

J) forward primer:
(SEQ ID NO: 19)
5'-GGAAGCAATACATATCTTAGAAATGAACTC-3', reverse primer:
(SEQ ID NO: 20)
5'-TCGGACAACTGCAAGCATCTAC-3';

K) forward primer:
(SEQ ID NO: 21)
5'-GAGTGAAAAAGATTTTGTTCAAGTTG-3', reverse primer:
(SEQ ID NO: 22)
5'-AAAAGTCGCTCAGGTTATGC-3';

L) forward primer:
(SEQ ID NO: 23)
5'-AGTGCCTGAACCTCAATTTG-3', reverse primer:
(SEQ ID NO: 24)
5'-TCGATAGGATTTTCTTCAAAATATTTAC-3';

M) forward primer:
(SEQ ID NO: 25)
5'-GTTTGGTACAGTTTATGGCATTTCAC-3', reverse primer:
(SEQ ID NO: 26)
5'-CATGGCAATATCAACAATACTCATCTTAC-3';

N) forward primer:
(SEQ ID NO: 27)
5'-CAGGAGCATGAGGTTCACAGTATG-3', reverse primer:
(SEQ ID NO: 28)
5'-TCTCTGGCCCCGCACAATG-3';

O) forward primer:
(SEQ ID NO: 29)
5'-GGGCTACAGAGATAGATATTACAGTAACTTAG-3',

-continued
reverse primer:
(SEQ ID NO: 30)
5'-CCACGGCTCTTCCCTCCAAG-3';

P) forward primer:
(SEQ ID NO: 31)
5'-TTCCGGTCGATCCTGCC-3', reverse primer:
(SEQ ID NO: 32)
5'-GTTGTCCTGAGCCGTCC-3';

Q) forward primer:
(SEQ ID NO: 33)
5'-AGACGATCCAGTTTGTATTAG-3', reverse primer:
(SEQ ID NO: 34)
5'GGCATCCTAACTCACTTAG-3';
and R) forward primer:
(SEQ ID NO: 35)
5'-TCTGGAAAACAATGTGTTC-3', reverse primer:
(SEQ ID NO: 36)
5'-GGCATGTCGATTCTAATTC-3'.

Preferred amplicons amplified in target organisms are listed in Table 6. However, a person skilled in the art knows that these amplicon sequences naturally vary in related strains. This minor variation can be taken into account while designing primers suitable to amplify said amplicons in the method of the present invention. Preferably, at least 20, 25, 30 or 35 nucleotides long sequence of each of the target amplicons selected from the group consisting of SEQ ID NOS:55-72, preferably SEQ ID NOS:61-63 and 65-68, are amplified in the method.

The method of the invention is characterized in that the presence of the amplified target sequence, i.e. the product, of each of primer pairs A) to R) in the PCR reaction in step iv) indicates the presence of diarrhoea causing pathogens in the sample in the following way:

the product of primer pair A) or B) indicates the presence of EHEC;
the product of primer pair C) indicates the presence of EHEC/EPEC;
the product of primer pair D) indicates the presence of *Salmonella*;
the product of primer pair E) or F) indicates the presence of *Shigella*/EIEC;
the product of primer pair G), H), or I) indicates the presence of ETEC;
the product of primer pair J) indicates the presence of EAEC;
the product of primer pair K) indicates the presence of *Campylobacter jejuni*;
the product of primer pair L) indicates the presence of *Campylobacter coli*;
the product of primer pair M) indicates the presence of *Yersinia enterocolitica/pseudotuberculosis*;
the product of primer pair N) indicates the presence of *Yersinia pseudotuberculosis/pestis*;
the product of primer pair O) indicates the presence of *Vibrio cholerae*:
the product of primer pair P) indicates the presence of *Giardia lamblia*;
the product of primer pair Q) indicates the presence of *Entamoeba histolytica*; and
the product of primer pair R) indicates the presence of *Cryptosporidium* sp.

Preferably, each primer of said primer pairs is less than 35, 40, 45, 50 or 55 nucleotides long, and more preferably, less than 50 nucleotides long. Each of the present primers can also be defined as consisting of at least 10 contiguous nucleotides present in one primer sequence selected from the group consisting of SEQ ID NOS:1-36.

One specific embodiment of the invention is to perform said method as a real-time polymerase chain reaction and in that case nucleic acid probes comprising or consisting of the following sequences are specifically used with each of primer pairs A) to R), preferably G) to I) and K) to N).

```
the probe for primer pair A):
                                      (SEQ ID NO: 37)
5'-TCCATGATARTCAGGCAGGACACTACTCAACCTTCC-3' the probe for primer pair B):
                                      (SEQ ID NO: 38)
5'-TTGTCACTGTCACAGCAGAAGCCTTACGC-3' the probe for primer pair C):
                                      (SEQ ID NO: 39)
5'-AGATTAACCTCTGCCGTTCCATAATGTTGTAACCA-3' the probe for primer pair D):
                                      (SEQ ID NO: 40)
5'-CCAAACCTAAAACCAGTAAAGGCGAGCAGC-3' the probe for primer pair E):
                                      (SEQ ID NO: 41)
5'-TCACTCCCGACACGCCATAGAAACGCATTT-3' the probe for primer pair F):
                                      (SEQ ID NO: 42)
5'-ACAAACAGCAAAAGAGCATAGCATCCGAGAACT-3' the probe for primer pair G):
                                      (SEQ ID NO: 43)
5'-CAAATATCCGTGAAACAACATGAC-3' the probe for primer pair H):
                                      (SEQ ID NO: 44)
5'-AGGATTACAACACAATTCACAGCAGT-3' the probe for primer pair I):
                                      (SEQ ID NO: 45)
5'-AGCAGGTTTCCCACCGGATCACCA-3' the probe for primer pair J):
                                      (SEQ ID NO: 46)
5'-TCCGTATATTATCATCAGGGCATCCTTTAGGCGT-3' the probe for primer pair K):
                                      (SEQ ID NO: 47)
5'-AAGACCCACAGTTTTACCAAGTTTT-3' the probe for primer pair L):
                                      (SEQ ID NO: 48)
5'-AACTTGGCTCTTCTTATGTGCGT-3' the probe for primer pair M):
                                      (SEQ ID NO: 49)
5'-CCTGGATAAGCGAGCGACGTATTCTCTATGC-3' the probe for primer pair N):
                                      (SEQ ID NO: 50)
5'-AAACCAAAGCCGCCCACACCACAG-3' the probe for primer pair O):
                                      (SEQ ID NO: 51)
5'-AACCTGCCAATCCATAACCATCTGCTGCTG-3' the probe for primer pair P):
                                      (SEQ ID NO: 52)
5'-ACGAAGCCATGCATGCCCGCT-3' the probe for primer pair Q):
                                      (SEQ ID NO: 53)
5'-ACAAAATGGCCAATTCATTCAATGAA-3' the probe for primer pair R):
                                      (SEQ ID NO: 54)
5'-CCTCCTAATCCAGAATGTCCTCCAG-3'
```

The melting temperature, Tm, of some of the probes (such as probes for primer pairs G), H), K) and L)) is preferably increased at least 5 degrees ° C. by addition of modified nucleotides. The amount of modified nucleotides in one probe is 1, 2, 3 or preferably 4. The underlined nucleotides in the above list are modified nucleotides each increasing the Tm of the probe. The modified nucleotide can be a LNA nucleotide (Exiqon A/S), minor groove binder (MGB™), SuperBase, or Peptide Nucleic Acid (PNA) or any other modification increasing the Tm of the probe.

Preferably, the above probes comprise the sequences as defined and are less than 40, 45, 50 or 55 nucleotides long, and more preferably, less than 50 nucleotides long. Each of the present probes can also be defined as consisting of at least 10 contiguous nucleotides present in one probe sequence selected from the group consisting of SEQ ID NOS:37-54.

The method of the invention is based on multiplex PCR technique, wherein primer pairs are divided into separate PCR reactions. As a general guideline the multiplex assay should be designed so that the most frequently appearing pathogens (e.g. Antikainen et al, 2009) are in different multiplex reactions.

In one embodiment, the invention provides nucleotide primers comprising or consisting of any of the primer sequences from primer pairs G) to I) and K) to N) as defined above.

In another embodiment, the invention provides nucleotide primer pairs comprising or consisting of the sequences from any of primer pairs G) to I) and K) to N) as defined above.

In a further embodiment, the invention provides nucleotide probes comprising or consisting of any of the probe sequences as defined above.

The present invention is preferably directed to a method for determining the presence of diarrhoea causing pathogens in a sample, wherein the presence of at least pathogens ETEC, *Campylobacter jejuni*, and *Campylobacter coli* is checked in said sample. Further target pathogens may be *Yersinia enterocolitica/pseudotuberculosis*, and *Yersinia pseudotuberculosis/pestis*.

The present invention is further directed to the use of nucleotide primers, primer pairs or probes as defined above for determining the presence of diarrhoea causing pathogens in a sample.

The present invention also provides kits for the detection of the presence of diarrhoea causing pathogens in a sample. Such a kit comprises primer pairs selected from the group consisting of primer pairs A) to R), preferably G) to I) and K) to N), as defined above. The kit may further comprise a probe selected from the probes as defined above. The use of the primer pairs and probes are described above and in the Example below. Preferably, said kit comprises means for a real-time polymerase chain reaction, such as labelled probes, polymerase enzymes, buffers and nucleotides. Preferably, said kit is for the detection of the presence of at least pathogens ETEC, *Campylobacter jejuni*, and *Campylobacter coli* in a sample.

The publications and other materials used herein to illuminate the background of the invention, and in particular, to provide additional details with respect to its practice, are incorporated herein by reference. The present invention is further described in the following example, which is not intended to limit the scope of the invention.

Example

Materials and Methods

Patient Samples.

Control stool samples were cultured at HUSLAB for *Salmonella, Yersinia, Shigella, Campylobacter* and EHEC with standard biochemical methods. A total of 146 travellers were recruited in Travel Clinic (Medicity, Helsinki, Finland) to participate in this study during six month period. The age ranged from 1 to 72 (mean 39.2 years); 84 (57.5%) were females and 62 (42.5%) were males. The travel destinations were Europe in 7.5%, Asia in 32.9%, Africa in 44.5%, Australia in 1.4% and America in 13.7% of cases.

Total nucleic acids were purified from the stool samples with NucliSENS kit using easyMAG platform as described in Antikainen et al., 2009. Briefly, stool swabs were suspended to 100 μl of Tris-EDTA buffer and purified by the general method of easyMAG platform and eluted to the volume of 25 p 1. Eluate (0.5 μl) was used as a template in PCR.

Alternatively, the swaps can be suspended directly into lysis buffer. The samples are eluted to a volume of 100 ul and 2 ul of eluate is used as a template in PCR. This protocol is suitable for fully automated, integrated sample preparation and PCR plate setup steps.

Identification of the Isolates.

Faecal samples positive in PCR for *Salmonella, Shigella, Yersinia, Campylobacter* and EHEC were cultured and identified with normal diagnostics methods. Since for diarrhoeal *E. coli* strains no cultivation based routine method exists, positive samples were analysed by previously developed multiplex-PCR (Antikainen et al., 2009).

From those samples of which isolation of bacterial strains was unsuccessful, corresponding genes were separately amplified and sequenced in Sequence Core Facility in Haartman Institute (Helsinki, Finland) using primers listed in Table 1. Sequences were identified by Basic Local Alignment Search Tool (BLAST, http://blast.ncbi.nlm.nih.gov/Blast.cgi).

Design of the Real-Time-PCR.

PCR was designed to identify specific virulence genes, species specific genes, or species specific regions within established universal genes (Table 1). Real-Time PCR primers and probes were designed with Allele ID and Beacon Designer software (Palo Alto, Calif.) to recognize correct target genes and their global variants, including BLAST search and secondary structure prediction using NCBI data base.

RT-PCR was performed on Mx3005P detection system (Agilent Technologies, Garden Grove, Calif.) and thermocycling conditions were 95° C. for 15 min, 40 cycles of 94° C. for 1 min and 60° C. for 1 min. Fluorescence was recorded at each annealing step. The 20-0 reaction contained 1× Qiagen Multitect NoROX master mix (Qiagen, Hilden, Germany), 1 μl of primer/probe mix (Tables 1 and 2) and 0.5 μl of template DNA.

Specificity of the PCR.

The analytical specificity of the PCR was analysed by using 249 bacterial strains as positive controls including *Salmonella, Shigella, Campylobacter, Yersinia* and *Vibrio* strains as well as diarrhoeal *E. coli* strains (Tables 1 and 2). The strains were originated from the Helsinki University Hospital Laboratory (HUSLAB), the National Institute of Health and Welfare (THL), and as a kind gift from M. Alexander Schmidt and Inga Benz (Westfälische Wilhelms-Universität, Münster, Germany), from Isabel Scaletsky (Universidade Federal de São Paulo, Brazil) as well as from Lin Thorstensen Brandal (The Norwegian Institute of Public Health, Norway). As negative controls, 243 bacterial strains from all major genera were used as described in Antikainen et al., 2009.

For PCR analysis, bacterial cells were collected to 100 μl of water, boiled for 15 minutes, centrifuged one minute 13 000 rpm and the supernatant (0.5 μl) was used in PCR reactions or bacterial DNA was purified with NucliSENS kit using easyMAG automatic nucleic acid purification platform as described by the manufacturer (bioMérieux, Marcy l'Etoile, France).

Analytical Sensitivity of the PCR.

To analyze sensitivity for clinical use, a mixture of DNAs containing all templates purified by easyMAG for each amplicon were diluted 10-fold and analyzed by PCR. In addition, the amplification of each reporter was separately analysed in 10-fold dilutions using boiled bacterial mass. Shortly, bacteria were grown on agar plates, collected to TE buffer and the viable count (colony forming unit (CFU)) was determined. Bacteria were diluted 10-folds and boiled for 15 minutes, centrifuged one minute 13 000 rpm and the supernatant (0.5 μl) was used in PCR reactions.

Clinical Sensitivity and Specificity.

The clinical specificity and sensitivity was analysed with clinical samples (n=119) known to be positive for *Salmonella, Shigella, Campylobacter, Yersinia* or EHEC by routine cultivation method in HUSLAB. In addition, 65 culture negative samples were analysed.

Results

Validation of the Real-Time-PCR Method.

The Real-Time PCR assay was optimized and validated using the reference strains including 249 positive strains and 243 strains belonging to other major genera (Table 5). All positive control strains were correctly identified and no false positive amplification was obtained. Thus, the assay achieved 100% analytical specificity.

The clinical specificity and sensitivity was analyzed from faecal samples obtained from routine diagnostics. The routine samples positive in *Salmonella* (n=50), *Campylobacter* (n=50), *Yersinia* (n=4) and *Shigella* (n=6) as well as EHEC (n=9) were analysed in PCR and all but one gave correct amplification (Table 5). In addition, 64 culture negative samples were analysed and none were positive for *Salmonella, Campylobacter, Yersinia* or *Shigella*. Diarrhoeal *E. coli* strains could not be identified with this method since no cultivation method exists. Thus, the clinical sensitivity of the assay was 99.2% and clinical specificity was 100%.

Analytical sensitivity of PCR was defined by 10-fold dilutions of the template DNA mixture analyzed by PCR. The sensitivity with 40 amplification cycles was 0.1 ng/ml for EHEC and *Salmonella* and for others the sensitivity was 1 ng/ml. In addition, the sensitivity was measured from DNA obtained with boiling the bacterial strain. In that assay, the limit of detection was 5-50 CFU per reaction. These results represent the lowest concentration required for correct identification (>90% positive).

Clinical Validation of the PCR.

The real time PCR method was utilized in the analysis of the faecal samples of 146 travellers before and after the trip abroad. The data is presented in Tables 3 and 4. All samples were positive with the internal control; no PCR inhibition was detected. Of the pre-trip samples, only three (2.1%) were positive and those were positive for EAEC. From these samples, the *E. coli* strain giving congruent PCR result was isolated. The most common findings were diarrhoeagenic *E. coli* strains (EPEC; 41.1%, EAEC; 38.4%, ETEC; 18.5%, EHEC; 7.5%), followed by *Campylobacter* (4.1%), *Salmonella* (2.1%) and *Shigella*/EIEC (1.4%).

All samples positive in *Campylobacter, Yersinia, Shigella, Salmonella* or EHEC were confirmed as positive either by cultivation or by sequencing of the PCR product Two or more findings were found from 45 patients.

Secretion of Diarrhoeagenic *E. coli* Species.

The kinetics of DEC was studied from 60 patients with no trip abroad in two months follow-up period. The same finding was found in seven out of 60 samples (four times EAEC, two times EPEC), different finding than previously was found from five patients, but all of these had travelled abroad during the follow-up period, whereas the other follow-up samples were negative. This kinetics is in line with other Enterobacteriaceae pathogens previously described.

A norovirus was detected in 5.5% patients suggesting that bacteria are predominant pathogens in traveller's diarrhoea.

Discussion

This is the first systematic follow-up study analyzing all major pathogens associated with traveller's diarrhoea using the new molecular methods. The study design allowed the inventors to follow the consequences of travelling to the tropical countries case by case as a normal sample prior to the trip was available. The most important achievement of the study was that all the major pathogens within the patient group were able to be identified using straight-forward modern methods, which eliminates inherent biases in comparison to results from different studies. As expected in high hygiene countries, such as Finland, there was a very low prevalence of diarrhoeal pathogens in the healthy individuals (2.1%). In a striking contrast, the inventors were able to identify a pathogen in 74% of symptomatic patients which is probably the best estimate of patients with traveller's diarrhoeal to date which confirms that virtually all the pathogens are imported, and they do not belong to normal flora of Finnish patients. All the diarrhoeal pathogens were more frequent in the symptomatic patients than asymptomatic individuals, including all the diarrhoeagenic *E. coli* species suggesting that they all are relevant diarrhoeal pathogens, and not just reflecting a disturbance in normal flora. Of the samples from symptomatic patients, 26% were negative in all studied bacterial pathogens. This study is in line with other recent studies suggesting that diarrhoeagenic *E. coli* species are the most predominant bacterial pathogens in the patients with traveller's diarrhoea.

The study covers all the major bacterial pathogens, excluding *Aeromonas* sp, *Plesiomonas*, enterotoxigenic *Bacteroides fragilis, Arcobacter* and DAEC. Their relative proportion is low based on previous studies, and their pathogenic role and incidence is not fully understood yet (von Graevenitz, 2007). The Real-Time PCR method recognizes virulence genes or species specific genes of the pathogens. For example to identify the virulent EAEC, aggR gene was chosen since it is the best characterized gene contributing to aggregative pattern and diarrhoeal symptoms (Monteiro et al., 2009); (Huang et al., 2007; Mohamed et al., 2007). To cover all the possible clinically relevant target species, it was necessary to screen multiple different target genes and their conserved regions for optimal sensitivity and specificity of the assay. For example it was impossible to detect the pathogenic species among *Yersinia* and *Campylobacter* families using only one primer-probe set. The assay sensitivity and specificity were high, app. 100%, compared to independent reference methods suggesting that it could be possible to replace stool culture as primary screening method to traveller's diarrhoea. In any case, the high proportion of DEC in the patients with diarrhoea suggests that at least they should be analyzed by the method capable to identify DEC, such as PCR.

The assay design allows identification of 13 pathogens simultaneously using control samples in optimal conditions. The inventors were able to identify up to four different pathogens from one patient sample demonstrating that multiple pathogens can be identified in parallel. This is in line with the fact that there are often multiple pathogens causing the disease. Nevertheless, a typical PCR reaction inherently favours the most abundant target. A false negative result is most likely when there are one or two highly abundant pathogens among with one very low copy pathogen within the same multiplex reaction. This option must be controlled by other methods, and/or re-sampling and a warning reported when applying this assay to any diagnostic purpose. To minimize the risk for false negative results, the multiplex composition was designed so that the most frequent pathogens were in the different multiplex reactions.

An internal positive control was tested with each sample to monitor presence of putative PCR inhibitors, but no inhibition was detected. This suggests that the semi-automated DNA extraction process is of sufficient quality, and it is suitable for stool pathogen analysis.

Taken together, this study is line with the other recent studies suggesting that diarrhoeagenic *E. coli* species are the predominant stool pathogens in traveller's diarrhoeae. Applying the new Real-Time PCR technology, they can be now successfully screened, among with the other stool pathogens, directly from stool samples.

TABLE 1

Primers.

| Origin | Gene | Forward primer (5'->3') | Reverse primer (5'->3') |
|---|---|---|---|
| Multiplex 1 | | | |
| EHEC | stx1 | GCGTTCTTATGTAATGACTGCTGAAG (SEQ ID NO: 1) | AGAAATTCTTCCTACACGAACAGAGTC (SEQ ID NO: 2) |
| EHEC | stx2 | TGCATCCAGAGCAGTTCTGC (SEQ ID NO: 3) | CGGCGTCATCGTATACACAGG (SEQ ID NO: 4) |
| EHEC/EPEC | eae | CCAGGCTTCGTCACAGTTGC (SEQ ID NO: 5) | CAGTGAACTACCGTCAAAGTTATTACC (SEQ ID NO: 6) |
| *Salmonella* | invA | GCTCTTCGGCACAAGTAATATCAAC (SEQ ID NO: 7) | TCTATTTTAAATTCCGTGAAGCAAAACG (SEQ ID NO: 8) |

TABLE 1-continued

Primers.

| Origin | Gene | Forward primer (5'->3') | Reverse primer (5'->3') |
|---|---|---|---|
| Oryza sativa, terminal flower gene | Ory (a control) | CTAATCCCAGCAACCCAACC (SEQ ID NO: 73) | CTAATCAATGTGAGACATATGATAGAAATC (SEQ ID NO: 74) |
| Multiplex 2 | | | |
| ETEC | est | AAAATTGCAAAATCCGTTTAACTAATC (SEQ ID NO: 13) | GACTGACTAAAAGAGGGGAAAG (SEQ ID NO: 14) |
| ETEC | est | TCCTGAAAGCATGAATAGTAGC (SEQ ID NO: 15) | TTATTAATAGCACCCGGTACAAG (SEQ ID NO: 16) |
| ETEC | elt | CCGGCAGAGGATGGTTACAG (SEQ ID NO: 17) | TTGATTGATATTCCCTGAGATATATTGTG (SEQ ID NO: 18) |
| Yersinia enterocolitica/ pseudotuberculosis | virF | GTTTGGTACAGTTTATGGCATTTCAC (SEQ ID NO: 25) | CATGGCAATATCAACAATACTCATCTTAC (SEQ ID NO: 26) |
| Yersinia pseudotuberculosis/ pestis | rumB | CAGGAGCATGAGGTTCACAGTATG (SEQ ID NO: 27) | TCTCTGGCCCCGCACAATG (SEQ ID NO: 28) |
| Campylobacter jejuni | rimM | GAGTGAAAAGATTTTGTTCAAGTTG (SEQ ID NO: 21) | AAAAGTCGCTCAGGTTATGC (SEQ ID NO: 22) |
| Campylobacter coli | gyrB | AGTGCCTGAACCTCAATTTG (SEQ ID NO: 23) | TCGATAGGATTTTCTTCAAAATATTTAC (SEQ ID NO: 24) |
| Oryza sativa, terminal flower gene | Ory (a control) | CTAATCCCAGCAACCCAACC (SEQ ID NO: 73) | CTAATCAATGTGAGACATATGATAGAAATC (SEQ ID NO: 74) |
| Multiplex 3 | | | |
| Shigella/EIEC | ipaH | TGGTCCATCAGGCATCAGAAGG (SEQ ID NO: 9) | GGCAGTGCGGAGGTCATTTG (SEQ ID NO: 10) |
| Shigella/EIEC | invE | TGTCTTTATAGGACATCCCTGATACTTTC (SEQ ID NO: 11) | TATCTACTCTTGATGCCAGAAAACTAGC (SEQ ID NO: 12) |
| EAEC | aggR | GGAAGCAATACATATCTTAGAAATGAACT (SEQ ID NO: 19) | CTCGGACAACTGCAAGCATCTAC (SEQ ID NO: 20) |
| Vibrio cholerae | ctx | GGGCTACAGAGATAGATATTACAGTAACTTCCACGGCTCTTCCCTCCAAG AG (SEQ ID NO: 29) | (SEQ ID NO: 30) |
| Oryza sativa, terminal flower gene | Ory (a control) | CTAATCCCAGCAACCCAACC (SEQ ID NO: 73) | CTAATCAATGTGAGACATATGATAGAAATC (SEQ ID NO: 74) |
| Multiplex 4 | | | |
| Giardia sp | 18S rRNA gene | TTCCGGTCGATCCTGCC (SEQ ID NO: 31) | GTTGTCCTGAGCCGTCC (SEQ ID NO: 32) |
| Entamoeba histolytica | 18S rRNA gene | AGACGATCCAGTTTGTATTAG (SEQ ID NO: 33) | GGCATCCTAACTCACTTAG (SEQ ID NO: 34) |
| Cryptosporidium sp. | cowp | TCTGGAAAACAATGTGTTC (SEQ ID NO: 35) | GGCATGTCGATTCTAATTC (SEQ ID NO: 36) |
| Oryza sativa, terminal flower gene | Ory (a control) | CTAATCCCAGCAACCCAACC (SEQ ID NO: 73) | CTAATCAATGTGAGACATATGATAGAAATC (SEQ ID NO: 74) |

TABLE 2

Probes for rtPCR.

| Origin | Gene | Probe (5'->3') (SEQ ID NOS: 37-54 and 75) | 5'modification of the probe | 3'modification of the probe |
|---|---|---|---|---|
| Multiplex 1 | | | | |
| EHEC | stx1 | TCCATGATARTCAGGCAGGACACTACTCAACCTTCC (SEQ ID NO: 37) | 6-FAM | BHQ-1 |
| EHEC | stx2 | TTGTCACTGTCACAGCAGAAGCCTTACGC (SEQ ID NO: 38) | 6-FAM | BHQ-1 |
| EHEC/EPEC | eae | AGATTAACCTCTGCCGTTCCATAATGTTGTAACCA (SEQ ID NO: 39) | JOE | BHQ-1 |
| Salmonella | invA | CCAAACCTAAAACCAGTAAAGGCGAGCAGC (SEQ ID NO: 40) | TXR | BHQ-2 |
| Oryza sativa, terminal flower gene | Ory (a control) | CCTGCACTGGTAAGCTATG (SEQ ID NO: 75) | CY5 | BHQ-2 |
| Multiplex 2 | | | | |
| ETEC | est | CAAATATCCGTGAAACAACATGAC (SEQ ID NO: 43) | 6-FAM | BHQ-1 |
| ETEC | est | AGGATTACAACACAATTCACAGCAGT (SEQ ID NO: 44) | 6-FAM | BHQ-1 |
| ETEC | elt | AGCAGGTTTCCCACCGGATCACCA (SEQ ID NO: 45) | 6-FAM | BHQ-1 |
| Yersinia enterocolitica/ pseudotuberculosis | virF | CCTGGATAAGCGAGCGACGTATTCTCTATGC (SEQ ID NO: 49) | JOE | BHQ-1 |
| Yersinia pseudotuberculosis/ pestis | rumB | AAACCAAAGCCGCCCACACCACAG (SEQ ID NO: 50) | JOE | BHQ-1 |
| Campylobacter jejuni | rimM | AAGACCCACAGTTTTACCAAGTTTT (SEQ ID NO: 47) | TXR | BHQ-2 |
| Campylobacter coli | gyrB | AACTTGGCTCTTCTTATGTGCGT (SEQ ID NO: 48) | TXR | BHQ-2 |
| Oryza sativa, terminal flower gene | Ory (a control) | CCTGCACTGGTAAGCTATG (SEQ ID NO: 75) | CY5 | BHQ-2 |
| Multiplex 3 | | | | |
| Shigella/EIEC | ipaH | TCACTCCCGACACGCCATAGAAACGCATTT (SEQ ID NO: 40) | 6-FAM | BHQ-1 |
| Shigella/EIEC | invE | ACAAACAGCAAAAGAGCATAGCATCCGAGAACT (SEQ ID NO: 42) | 6-FAM | BHQ-1 |
| EAEC | aggR | TCCGTATATTATCATCAGGGCATCCTTTAGGCGT (SEQ ID NO: 46) | JOE | BHQ-1 |
| Vibrio cholerae | ctx | AACCTGCCAATCCATAACCATCTGCTGCTG (SEQ ID NO: 51) | TXR | BHQ-2 |
| Oryza sativa, terminal flower gene | Ory (a control) | CCTGCACTGGTAAGCTATG (SEQ ID NO: 75) | CY5 | BHQ-2 |
| Multiplex 4 | | | | |
| Giardia sp | 18S rRNA gene | ACGAAGCCATGCATGCCCGCT (SEQ ID NO: 52) | 6-FAM | BHQ-1 |

TABLE 2-continued

Probes for rtPCR.

| Origin | Gene | Probe (5'->3') (SEQ ID NOS: 37-54 and 75) | 5'modification of the probe | 3'modification of the probe |
|---|---|---|---|---|
| Entamoeba histolytica | 18S rRNA gene | ACAAAATGGCCAATTCATTCAATGAA (SEQ ID NO: 53) | JOE | BHQ-1 |
| Cryptosporidium sp. | cowp | CCTCCTAATCCAGAATGTCCTCCAG (SEQ ID NO: 54) | TXR | BHQ-2 |
| Oryza sativa, terminal flower gene | Ory (a control) | CCTGCACTGGTAAGCTATG (SEQ ID NO: 75) | CY5 | BHQ-2 |

TABLE 3

Findings before and after the trip abroad.

|  | Before trip abroad number (%) | After trip abroad number (%) |
|---|---|---|
| Campylobacter | 0 (0) | 6 (4.1) |
| Salmonella | 0 (0) | 3 (2.1) |
| Shigella/EIEC | 0 (0) | 2 (1.4) |
| Yersinia | 0 (0) | 0 (0) |
| EHEC | 0 (0) | 11 (7.5) |
| EAEC | 3 (2.1) | 56 (38.4) |
| EPEC | 0 (0) | 60 (41.1) |
| ETEC | 0 (0) | 27 (18.5) |
| Vibrio | 0 (0) | 0 (0) |
| Total | 3 (2.1) | 165 (113.0) |

TABLE 4

Findings after trip abroad with or without symptoms.

|  | asymptomatic number (%) | symptomatic number (%) |
|---|---|---|
| Campylobacter | 0 (0) | 6 (4.1) |
| Salmonella | 1 (0.7) | 2 (1.4) |
| Shigella/EIEC | 0 (0) | 2 (1.4) |
| Yersinia | 0 (0) | 0 (0) |
| Vibrio | 0 (0) | 0 (0) |
| EHEC | 4 (2.7) | 7 (4.8) |
| EAEC | 15 (10.3) | 40 (27.4) |
| EPEC | 19 (13.0) | 39 (26.7) |
| ETEC | 5 (3.4) | 22 (15.1) |
| Total | 31 (60.8) | 69 (74.2) |

TABLE 5

A summary of known positive control strains and samples.

|  | PCR positive | Total |
|---|---|---|
| Pure control strains |  |  |
| Positive control strains | 246 | 246 |
| Negative control strains | 0 | 243 |
| Total |  | 489 |
| Feacal control samples Positive |  |  |
| Campylobacter | 52 | 53 |
| Salmonella | 50 | 50 |
| Yersinia | 5 | 5 |
| Shigella | 6 | 6 |
| EHEC | 9 | 9 |
| Negative | 0 | 65 |

TABLE 6

Amplicons (5'->3') amplified in target organisms.

EHEC stx1

GCGTTCTTATGTAATGACTGCTGAAGATGTTGATCTTACATTGAACTGGGGAAGGTTGAGTAGTG
TCCTGCCTGATTATCATGGACAAGACTCTGTTCGTGTAGGAAGAATTTCT
(SEQ ID NO: 55)

EHEC stx2

TGCATCCAGAGCAGTTCTGCGTTTTGTCACTGTCACAGCAGAAGCCTTACGCTTCAGGCAGATACA
GAGAGAATTTCGTCAGGCACTGTCTGAAACTGCTCCTGTGTATACGATGACGCCG
(SEQ ID NO: 56)

TABLE 6-continued

Amplicons (5'->3') amplified in target organisms.

EHEC/EPEC eae

CCAGGCTTCGTCACAGTTGCAGGCCTGGTTACAACATTATGGAACGGCAGAGGTTAATCTGCAGA
GTGGTAATAACTTTGACGGTAGTTCACTG
(SEQ ID NO: 57)

*Salmonella* invA

GCTCTTCGGCACAAGTAATATCAACGGTACAGTCTCTGTAGAGACTTTATCGAGATCGCCAATCA
GTCCTAACGACGACCCTTCTTTTTCCTCAATACTGAGCGGCTGCTCGCCTTTGCTGGTTTTAGGTTT
GGCGGCGCTACGTTTTGCTTCACGGAATTTAAAATAGA
(SEQ ID NO: 58)

*Shigella*/EIEC ipaH

TGGTCCATCAGGCATCAGAAGGCCTTTTCGATAATGATACCGGCGCTCTGCTCTCCCTGGGCAGG
GAAATGTTCCGCCTCGAAATTCTGGAGGACATTGCCCGGGATAAAGTCAGAACTCTCCATTTTGT
GGATGAGATAGAAGTCTACCTGGCCTTCCAGACCATGCTCGCAGAGAAACTTCAGCTCTCCACTG
CCGTGAAGGAAATGCGTTTCTATGGCGTGTCGGGAGTGACAGCAAATGACCTCCGCACTGCC
(SEQ ID NO: 59)

*Shigella*/EIEC invE

TGTCTTTATAGGACATCCCTGATACTTTCAGAAAATTAAGACCAATACCAAGTTCTCGGATGCTAT
GCTCTTTTGCTGTTTGTATATCGTTTGCTAGTTTTCTGGCATCAAGAGTAGATA
(SEQ ID NO: 60)

ETEC est

AAAATTGCAAAATCCGTTTAACTAATCTCAAATATCCGTGAAACAACATGACGGGAGGTAACATG
AAAAAGCTAATGTTGGCAATTTTTATTTCTGTATTATCTTTCCCCTCTTTTAGTCAGTC
(SEQ ID NO: 61)

ETEC est

TCCTGAAAGCATGAATAGTAGCAATTACTGCTGTGAATTGTGTTGTAATCCTGCTTGTACCGGGTG
CTATTAATAA
(SEQ ID NO: 62)

ETEC elt

CCGGCAGAGGATGGTTACAGATTAGCAGGTTTCCCACCGGATCACCAAGCTTGGAGAGAAGAAC
CCTGGATTCATCATGCACCACAAGGTTGTGGAAATTCATCAAGAACAATTACAGGTGATACTTGT
AATGAGGAGACCCAGAATCTGAGCACAATATATCTCAGGGAATATCAATCAA
(SEQ ID NO: 63)

EAEC aggR

GGAAGCAATACATATCTTAGAAATGAACTCATATTTCTTGAGAGAGGAATAAATATATCAGTAAG
ATTGCAAAAGAAGAAATCAACAGTAAATCCATTTATCGCAATCAGATTAAGCAGCGATACATTAA
GACGCCTAAAGGATGCCCTGATGATAATATACGGAATATCAAAAGTAGATGCTTGCAGTTGTCCG
A (SEQ ID NO: 64)

*Campylobacter jejuni* rimM

GAGTGAAAAAGATTTTGTTCAAGTTGCAAAACTTGGTAAAACTGTGGGTCTTAAGGGTTATGTAA
AATTGCATAACCTGAGCGACTTTT (SEQ ID NO: 65)

*Campylobacter coli* gyrB

AGTGCCTGAACCTCAATTTGAAGGACAAACTAAAGGAAAACTTGGCTCTTCTTATGTGCGTCCTAT
AGTTTCAAAAGCAAGTTTTGAATATCTTAGTAAATATTTTGAAGAAAATCCTATCGA
(SEQ ID NO: 66)

*Yersinia enterocolitica/pseudotuberculosis* virF

GTTTGGTACAGTTTATGGCATTTCACCACGCGCCTGGATAAGCGAGCGACGTATTCTCTATGCTCA
CCAATTACTTCTTAATTGTAAGATGAGTATTGTTGATATTGCCATG (SEQ ID NO: 67)

*Yersinia pseudotuberculosis/pestis* rumB

CAGGAGCATGAGGTTCACAGTATGTGGGATCTGTTCTGTGGTGTGGGCGGCTTTGGTTTACATTG
TGCGGGGCCAGAGA (SEQ ID NO: 68)

TABLE 6-continued

Amplicons (5'->3') amplified in target organisms.

*Vibrio cholerae* ctx

GGGCTACAGAGATAGATATTACAGTAACTTAGATATTGCTCCAGCAGCAGATGGTTATGGATTGG
CAGGTTTCCCTCCGGAGCATAGAGCTTGGAGGGAAGAGCCGTGG (SEQ ID NO: 69)

*Giardia lamblia* 18S rRNA gene

TTCCGGTCGATCCTGCCGGAATCCGACGCTCTCCCCAAGGACACAAGCCATGCATGCCCGCGCAC
CCGGGAGGCGGCGGACGGCTCAGGACAAC (SEQ ID NO: 70)

*Entamoeba histolytica* 18S rRNA gene

AGACGATCCAGTTTGTATTAGTACAAAATGGCCAATTTATTTAAATGAATTGAGAAATGACATTCT
AAGTGAGTTAGGATGCC (SEQ ID NO: 71)

*Cryptosporidium sp.* cowp

TCTGGAAAACAATGTGTTCAATCAGACACAGCTCCTCCTAATCCAGAATGTCCTCCAGGCACTATA
CTGGAGAATGGCACATGTAAATTAATTCAACAAATTGATACCGTTTGTCCTTCTGGTTTTGTTGAA
GAAGGAAATAGATGTGTTCAATATCTCCCTGCAAATAAAATCTGTCCTCCTGGATTCAATTTGTCA
GGACAACAATGTATGGCACCAGAATCAGCTGAATTAGAATCGACATGCC
(SEQ ID NO: 72)

TABLE 7

Primers and a probe for *Oryza sativa*, terminal flower gene control

| | |
|---|---|
| CTAATCCCAGCAACCCAACC | (SEQ ID NO: 73) |
| CTAATCAATGTGAGACATATGATAGAAATC | (SEQ ID NO: 74) |
| CCTGCACTGGTAAGCTATG | (SEQ ID NO: 75) |

TABLE 8

Distribution of ETEC toxin variants in control strains and patient samples. The results show that all ETEC variants are detected by at least one of the present primer pairs.

| | | Oligonucleotide pairs amplifying the target (strain/patient sample) | | |
|---|---|---|---|---|
| Strain name | Origin | ST variant 1 est_005 (SEQ ID NOS: 13 and 14) | ST variant 2 estlab_004 (SEQ ID NOS: 15 and 16) | Heat labile toxin (LT) elt_001 (SEQ ID NOS: 17 and 18) |
| JA4 | Reference strain THL | − | + | + |
| JA24 | Reference strain THL | − | − | + |
| JA25 | Reference strain THL | − | − | + |
| JA26 | Reference strain THL | − | − | + |
| JA27 | Reference strain THL | − | − | + |
| JA28 | Reference strain THL | − | − | + |
| JA32 | Reference strain THL | − | + | − |
| JA35 | Control species, Germany | + | − | + |
| JA36 | Control species, Germany | + | − | + |
| JA48 | Patient sample | − | + | + |
| JA50 | Patient sample | + | − | − |
| JA53 | Patient sample | − | + | − |
| JA58 | Patient sample | + | − | − |
| JA61 | Patient sample | + | − | − |
| JA64 | Patient sample | − | + | + |
| JA85 | Patient sample | + | − | − |
| JA88 | Patient sample | − | + | − |
| JA122 | Patient sample | + | − | − |
| JA124 | Patient sample | − | + | + |
| mixB | control DNA mixture | + | + | + |

ST = Heat Stable Toxin
LT = Heat Labile Toxin

REFERENCES

Allos, B. M. (2001). *Campylobacter jejuni* Infections: update on emerging issues and trends. Clin. Infect. Dis. 32, 1201-1206.

Antikainen, J., Tarkka, E., Haukka, K., Siitonen, A., Vaara, M., and Kirveskari, J. (2009). New 16-plex PCR method for rapid detection of diarrhoeagenic *Escherichia coli* directly from stool samples. Eur. J. Clin. Microbiol. Infect. Dis. 28, 899-908.

Aranda, K. R., Fagundes-Neto, U., and Scaletsky, I. C. (2004). Evaluation of multiplex PCRs for diagnosis of infection with diarrhoeagenic *Escherichia coli* and *Shigella* spp. J. Clin. Microbiol. 42, 5849-5853.

Bottone, E. J. (1999). *Yersinia enterocolitica*: overview and epidemiologic correlates. Microbes Infect. 1, 323-333.

Brandal, L. T., Lindstedt, B. A., Aas, L., Stavnes, T. L., Lassen, J., and Kapperud, G. (2007). Octaplex PCR and fluorescence-based capillary electrophoresis for identification of human diarrhoeagenic *Escherichia coli* and *Shigella* spp. J. Microbiol. Methods 68, 331-341.

Chen, H. D., and Frankel, G. (2005). Enteropathogenic *Escherichia coli*: unravelling pathogenesis. FEMS Microbiol. Rev. 29, 83-98.

Coburn, B., Grassl, G. A., and Finlay, B. B. (2007). *Salmonella*, the host and disease: a brief review. Immunol. Cell Biol. 85, 112-118.

Flores, J., and Okhuysen, P. C. (2009). Enteroaggregative *Escherichia coli* infection. Curr. Opin. Gastroenterol. 25, 8-11.

El Tahir Y, Skurnik M. (2001) YadA, the multifaceted *Yersinia* adhesin. Int J Med Microbiol. 291:209-218.

Guion, C. E., Ochoa, T. J., Walker, C. M., Barletta, F., and Cleary, T. G. (2008). Detection of diarrhoeagenic *Escherichia coli* by use of melting-curve analysis and real-time multiplex PCR. J. Clin. Microbiol. 46, 1752-1757.

Huang, D. B., Mohamed, J. A., Nataro, J. P., DuPont, H. L., Jiang, Z. D., and Okhuysen, P. C. (2007). Virulence characteristics and the molecular epidemiology of enteroaggregative *Escherichia coli* isolates from travellers to developing countries. J. Med. Microbiol. 56, 1386-1392.

Karch, H., Tarr, P. I., and Bielaszewska, M. (2005). Enterohaemorrhagic *Escherichia coli* in human medicine. Int. J. Med. Microbiol. 295, 405-418.

Kimata, K., Shima, T., Shimizu, M., Tanaka, D., Isobe, J., Gyobu, Y., Watahiki, M., and Nagai, Y. (2005). Rapid categorization of pathogenic *Escherichia coli* by multiplex PCR. Microbiol. Immunol. 49, 485-492.

Lan, R., and Reeves, P. R. (2002). *Escherichia coli* in disguise: molecular origins of *Shigella*. Microbes Infect. 4, 1125-1132.

Mohamed, J. A., Huang, D. B., Jiang, Z. D., DuPont, H. L., Nataro, J. P., Belkind-Gerson, J., and Okhuysen, P. C. (2007). Association of putative enteroaggregative *Escherichia coli* virulence genes and biofilm production in isolates from travelers to developing countries. J. Clin. Microbiol. 45, 121-126.

Monteiro, B. T., Campos, L. C., Sircili, M. P., Franzolin, M. R., Bevilacqua, L. F., Nataro, J. P., and Elias, W. P. (2009). The dispersin-encoding gene (aap) is not restricted to enteroaggregative *Escherichia coli*. Diagn. Microbiol. Infect. Dis. 65, 81-84.

Müller, D., Greune, L., Heusipp, G., Karch, H., Fruth, A., Tschape, H., and Schmidt, M. A. (2007). Identification of unconventional intestinal pathogenic *Escherichia coli* isolates expressing intermediate virulence factor profiles by using a novel single-step multiplex PCR. Appl. Environ. Microbiol. 73, 3380-3390.

Nelson, E. J., Harris, J. B., Morris, J. G., Jr, Calderwood, S. B., and Camilli, A. (2009). Cholera transmission: the host, pathogen and bacteriophage dynamic. Nat. Rev. Microbiol. 7, 693-702.

Parsot, C. (2005). *Shigella* spp. and enteroinvasive *Escherichia coli* pathogenicity factors. FEMS Microbiol. Lett. 252, 11-18.

Poly, F., and Guerry, P. (2008). Pathogenesis of *Campylobacter*. Curr. Opin. Gastroenterol. 24, 27-31.

Qadri, F., Svennerholm, A. M., Faruque, A. S., and Sack, R. B. (2005). Enterotoxigenic *Escherichia coli* in developing countries: epidemiology, microbiology, clinical features, treatment, and prevention. Clin. Microbiol. Rev. 18, 465-483.

Vidal, M., Kruger, E., Duran, C., Lagos, R., Levine, M., Prado, V., Toro, C., and Vidal, R. (2005). Single multiplex PCR assay to identify simultaneously the six categories of diarrhoeagenic *Escherichia coli* associated with enteric infections. J. Clin. Microbiol. 43, 5362-5365.

Vidal, R., Vidal, M., Lagos, R., Levine, M., and Prado, V. (2004). Multiplex PCR for diagnosis of enteric infections associated with diarrhoeagenic *Escherichia coli*. J. Clin. Microbiol. 42, 1787-1789.

von Graevenitz, A. (2007). The role of *Aeromonas* in diarrhoea: a review. Infection 35, 59-64.

---

The invention claimed is:

1. A method for determining the presence of diarrhoea causing pathogens in a biological sample comprising the steps of:
   i) performing a multiplex polymerase chain reaction on the biological sample or nucleic acid isolated therefrom with multiplex primer pairs, wherein the multiplex primer pairs comprise ETEC primer pairs that amplify a nucleic acid sequence (g) of the ETEC amplicon consisting of SEQ ID NO:61, a nucleic acid sequence (h) of the ETEC amplicon consisting of SEQ ID NO:62, and a nucleic acid sequence (i) of the ETEC amplicon consisting of SEQ ID NO:63, wherein each of said multiplex primer pairs recognizes and binds to one of said ETEC amplicons consisting of SEQ ID NO:61, 62 or 63, and wherein the multiplex primer pairs comprise *Campylobacter* primer pairs that amplify a nucleic acid sequence (k) of the *Campylobacter* amplicon consisting of SEQ ID NO:65, and a nucleic acid sequence (l) of the *Campylobacter* amplicon consisting of SEQ ID NO:66; and
   ii) detecting for amplification of the nucleic acid sequences (g), (h), (i), (k) and (l), wherein the amplification of any of the nucleic acid sequences (g), (h) and (i) is indicative of the presence of diarrhoea causing pathogen ETEC in the biological sample, and wherein the amplification of any of the nucleic acid sequences (k) and (l) is indicative of the presence of diarrhea causing pathogen *Campylobacter* in the biological sample.

2. The method according to claim 1, wherein step i) further comprises primer pairs which amplify each of the *Yersinia* amplicons comprising SEQ ID NOS: 67-68.

3. The method according to claim 1, wherein in step i) the sample or isolated nucleic acid therefrom is contacted with at least one ETEC primer pair selected from the group consisting of a nucleic acid sequence (g1) of at least 10 consecutive nucleotides of the sequence consisting of SEQ ID NO:13 and a nucleic acid sequence (g2) of at least 10 consecutive nucleotides of the sequence consisting of SEQ ID NO:14; a nucleic acid sequence (h1) of at least 10 consecutive nucleotides of the sequence consisting of SEQ ID NO:15 and a nucleic acid sequence (h2) of at least 10 consecutive nucleotides of the sequence consisting of SEQ ID NO:16; and a nucleic acid sequence (i1) of at least 10 consecutive nucleotides of the sequence consisting of SEQ ID NO: 17 and a nucleic acid sequence (i2) of at least 10 consecutive nucleotides of the sequence consisting of SEQ ID NO:18.

4. The method according to claim 1, wherein said multiplex primer pairs are selected from the group consisting of a nucleic acid sequence (k1) of at least 10 consecutive nucleotides of the sequence consisting of SEQ ID NO:21 and a nucleic acid sequence (k2) of at least 10 consecutive nucleotides of the sequence consisting of SEQ ID NO:22; and a nucleic acid sequence (l1) of at least 10 consecutive nucleotides of the sequence consisting of SEQ ID NO:23 and a nucleic acid sequence (l2) of at least 10 consecutive nucleotides of the sequence consisting of SEQ ID NO:24.

5. The method according to claim 1, wherein in step i) the sample or isolated nucleic acid therefrom is contacted with further primer pairs comprising at least one of the following sequences or a primer consisting of at least 10 contiguous nucleotides present in at least one of the following sequences:

A) forward primer:
                                             (SEQ ID NO: 1)
5'-GCGTTCTTATGTAATGACTGCTGAAG-3', reverse primer:
                                             (SEQ ID NO: 2)
5'-AGAAATTCTTCCTACACGAACAGAGTC-3';

B) forward primer:
                                             (SEQ ID NO: 3)
5'-TGCATCCAGAGCAGTTCTGC-3', reverse primer:
                                             (SEQ ID NO: 4)
5'-CGGCGTCATCGTATACACAGG-3';

-continued

C) forward primer:
(SEQ ID NO: 5)
5'-CCAGGCTTCGTCACAGTTGC-3', reverse primer:
(SEQ ID NO: 6)
5'-CAGTGAACTACCGTCAAAGTTATTACC-3';

D) forward primer:
(SEQ ID NO: 7)
5'-GCTCTTCGGCACAAGTAATATCAAC-3', reverse primer:
(SEQ ID NO: 8)
5'-TCTATTTTAAATTCCGTGAAGCAAAACG-3';

E) forward primer:
(SEQ ID NO: 9)
5'-TGGTCCATCAGGCATCAGAAGG-3', reverse primer:
(SEQ ID NO: 10)
5'-GGCAGTGCGGAGGTCATTTG-3';

F) forward primer:
(SEQ ID NO: 11)
5'-TGTCTTTATAGGACATCCCTGATACTTTC-3', reverse primer:
(SEQ ID NO: 12)
5'-TATCTACTCTTGATGCCAGAAAACTAGC-3';

J) forward primer:
(SEQ ID NO: 19)
5'-GGAAGCAATACATATCTTAGAAATGAACTC-3', reverse primer:
(SEQ ID NO: 20)
5'-TCGGACAACTGCAAGCATCTAC-3';

M) forward primer:
(SEQ ID NO: 25)
5'-GTTTGGTACAGTTTATGGCATTTCAC-3', reverse primer:
(SEQ ID NO: 26)
5'-CATGGCAATATCAACAATACTCATCTTAC-3';

N) forward primer:
(SEQ ID NO: 27)
5'-CAGGAGCATGAGGTTCACAGTATG-3', reverse primer:
(SEQ ID NO: 28)
5'-TCTCTGGCCCCGCACAATG-3';

O) forward primer:
(SEQ ID NO: 29)
5'-GGGCTACAGAGATAGATATTACAGTAACTTAG-3', reverse primer:
(SEQ ID NO: 30)
5'-CCACGGCTCTTCCCTCCAAG-3';

P) forward primer:
(SEQ ID NO: 31)
5'-TTCCGGTCGATCCTGCC-3', reverse primer:
(SEQ ID NO: 32)
5'-GTTGTCCTGAGCCGTCC-3';

Q) forward primer:
(SEQ ID NO: 33)
5'-AGACGATCCAGTTTGTATTAG-3', reverse primer:
(SEQ ID NO: 34)
5'-GGCATCCTAACTCACTTAG-3';
and R) forward primer:
(SEQ ID NO: 35)
5'-TCTGGAAAACAATGTGTTC-3', reverse primer:
(SEQ ID NO: 36)
5'-GGCATGTCGATTCTAATTC-3'.

6. The method according to claim 3, wherein the presence of the amplified target C sequence, of each of primer pairs in the PCR reaction indicates the presence of diarrhoea causing pathogens in the sample in the following way:
the product of primer pair A) or B) indicates the presence of EHEC;
the product of primer pair C) indicates the presence of EHEC/EPEC;
the product of primer pair D) indicates the presence of *Salmonella;*
the product of primer pair E) or F) indicates the presence of *Shigella*/EIEC;
the product of primer pair G), H), or I) indicates the presence of ETEC;
the product of primer pair J) indicates the presence of EAEC;
the product of primer pair K) indicates the presence of *Campylobacter jejuni;*
the product of primer pair L) indicates the presence of *Campylobacter coli;*
the product of primer pair M) indicates the presence of *Yersinia enterocolitica/pseudotuberculosis;*
the product of primer pair N) indicates the presence of *Yersinia pseudotuberculosis/pestis;*
the product of primer pair O) indicates the presence of *Vibrio cholerae:*
the product of primer pair P) indicates the presence of *Giardia lamblia;*
the product of primer pair Q) indicates the presence of *Entamoeba histolytica;* and
the product of primer pair R) indicates the presence of *Cryptosporidium* sp.

7. The method according to claim 1, wherein said biological sample is a stool sample or a food sample.

8. The method according to claim 5, wherein said multiplex PCR assay is performed as a real-time polymerase chain reaction and probes consisting of at least 10 contiguous nucleotides present in the following sequences are specifically used with each of primer pairs:

the probe for primer pair A):
(SEQ ID NO: 37)
5'-TCCATGATARTCAGGCAGGACACTACTCAACCTTCC-3', the probe for primer pair B):
(SEQ ID NO: 38)
5'-TTGTCACTGTCACAGCAGAAGCCTTACGC-3', the probe for primer pair C):
(SEQ ID NO: 39)
5'-AGATTAACCTCTGCCGTTCCATAATGTTGTAACCA-3', the probe for primer pair D):
(SEQ ID NO: 40)
5'-CCAAACCTAAAACCAGTAAAGGCGAGCAGC-3',

```
the probe for primer pair E):
                                              (SEQ ID NO: 41)
5'-TCACTCCCGACACGCCATAGAAACGCATTT-3', the probe for primer pair F):
                                              (SEQ ID NO: 42)
5'-ACAAACAGCAAAAGAGCATAGCATCCGAGAACT-3', the probe for primer pair G):
                                              (SEQ ID NO: 43)
5'-CAAATATCCGTGAAACAACATGAC-3', the probe for primer pair H):
                                              (SEQ ID NO: 44)
5'-AGGATTACAACACAATTCACAGCAGT-3', the probe for primer pair I):
                                              (SEQ ID NO: 45)
5'-AGCAGGTTTCCCACCGGATCACCA-3', the probe for primer pair J):
                                              (SEQ ID NO: 46)
5'-TCCGTATATTATCATCAGGGCATCCTTTAGGCGT-3', the probe for primer pair K):
                                              (SEQ ID NO: 47)
5'-AAGACCCACAGTTTTACCAAGTTTT-3', the probe for primer pair L):
                                              (SEQ ID NO: 48)
5'-AACTTGGCTCTTCTTATGTGCGT-3', the probe for primer pair M):
                                              (SEQ ID NO: 49)
5'-CCTGGATAAGCGAGCGACGTATTCTCTATGC-3', the probe for primer pair N):
                                              (SEQ ID NO: 50)
5'-AAACCAAAGCCGCCCACACCACAG-3', the probe for primer pair O):
                                              (SEQ ID NO: 51)
5'-AACCTGCCAATCCATAACCATCTGCTGCTG-3', the probe for primer pair P):
                                              (SEQ ID NO: 52)
5'-ACGAAGCCATGCATGCCCGCT-3', the probe for primer pair Q):
                                              (SEQ ID NO: 53)
5'-ACAAAATGGCCAATTCATTCAATGAA-3', the probe for primer pair R):
                                              (SEQ ID NO: 54)
5'-CCTCCTAATCCAGAATGTCCTCCAG-3',
``` wherein the probes comprise modified nucleotides increasing melting temperature, Tm, of the probes.

9. The method according to claim 5, wherein primer pairs A) to F) and G) to N) are in separate PCR reactions.

10. The method according to claim 5, wherein the method comprises the following PCR reactions: the first reaction with primer pairs A) to D), the second reaction with primer pairs K) to L), the third reaction with primer pairs E), F), M), N) and O) and the fourth reaction with primer pairs P) to R).

11. The method according to claim 5, wherein the method comprises the following PCR reactions: the first reaction with primer pairs A) to D), the second reaction with primer pairs G) to I) and K) to N), the third reaction with primer pairs E), F), J) and O) and the fourth reaction with primer pairs P) to R).

12. The method according to claim 3, wherein the at least one ETEC primer pair comprises a primer consisting of SEQ ID NO: 13, 14, 15, 16, 17 or 18.

13. The method according to claim 12, wherein the at least one ETEC primer pair consists of the primers consisting of SEQ ID NOS: 13 and 14.

14. The method according to claim 12, wherein the at least one ETEC primer pair consists of the primers consisting of SEQ ID NOS: 15 and 16.

15. The method according to claim 12, wherein the at least one ETEC primer pair consists of the primers consisting of SEQ ID NOS: 17 and 18.

16. The method according to claim 4, wherein the at least one *Campylobacter* primer pair comprises a primer consisting of SEQ ID NO: 21, 22, 23 or 24.

17. The method according to claim 16, wherein the at least one *Campylobacter* primer pair consists of the primers consisting of SEQ ID NOS: 21 and 22.

18. The method according to claim 16, wherein the at least one *Campylobacter* primer pair consists of the primers consisting of SEQ ID NOS: 23 and 24.

19. The method according to claim 5, wherein said multiplex PCR assay is performed as a real-time polymerase chain reaction and probes comprising the following sequences are specifically used with each of primer pairs:

```
the probe for primer pair A):
                                              (SEQ ID NO: 37)
5'-TCCATGATARTCAGGCAGGACACTACTCAACCTTCC-3', the probe for primer pair B):
                                              (SEQ ID NO: 38)
5'-TTGTCACTGTCACAGCAGAAGCCTTACGC-3', the probe for primer pair C):
                                              (SEQ ID NO: 39)
5'-AGATTAACCTCTGCCGTTCCATAATGTTGTAACCA-3', the probe for primer pair D):
                                              (SEQ ID NO: 40)
5'-CCAAACCTAAAACCAGTAAAGGCGAGCAGC-3', the probe for primer pair E):
                                              (SEQ ID NO: 41)
5'-TCACTCCCGACACGCCATAGAAACGCATTT-3', the probe for primer pair F):
                                              (SEQ ID NO: 42)
5'-ACAAACAGCAAAAGAGCATAGCATCCGAGAACT-3', the probe for primer pair G):
                                              (SEQ ID NO: 43)
5'-CAAATATCCGTGAAACAACATGAC-3', the probe for primer pair H):
                                              (SEQ ID NO: 44)
5'-AGGATTACAACACAATTCACAGCAGT-3', the probe for primer pair I):
                                              (SEQ ID NO: 45)
5'-AGCAGGTTTCCCACCGGATCACCA-3', the probe for primer pair J):
                                              (SEQ ID NO: 46)
5'-TCCGTATATTATCATCAGGGCATCCTTTAGGCGT-3', the probe for primer pair K):
                                              (SEQ ID NO: 47)
5'-AAGACCCACCGTTTTACCAAGTTTT-3', the probe for primer pair L):
                                              (SEQ ID NO: 48)
5'-AACTTGGCTCTTCTTATGTGCGT-3', the probe for primer pair M):
                                              (SEQ ID NO: 49)
5'-CCTGGATAAGCGAGCGACGTATTCTCTATGC-3', the probe for primer pair N):
                                              (SEQ ID NO: 50)
5'-AAACCAAAGCCGCCCACACCACAG-3',
```

-continued the probe for primer pair O):
(SEQ ID NO: 51)
5'-AACCTGCCAATCCATAACCATCTGCTGCTG-3', the probe for primer pair P):
(SEQ ID NO: 52)
5'-ACGAAGCCATGCATGCCCGCT-3', the probe for primer pair Q):
(SEQ ID NO: 53)
5'-ACAAAATGGCCAATTCATTCAATGAA-3', the probe for primer pair R):
(SEQ ID NO: 54)
5'-CCTCCTAATCCAGAATGTCCTCCAG-3', wherein the probes comprise modified nucleotides increasing melting temperature, Tm, of the probes.

* * * * *

SEQUENCE LISTING

```
<160> NUMBER OF SEQ ID NOS: 75

<210> SEQ ID NO 1
<211> LENGTH: 26
<212> TYPE: DNA
<213> ORGANISM: Artificial Sequence
<220> FEATURE:
<223> OTHER INFORMATION: Synthetic: PCR primer

<400> SEQUENCE: 1
gcgttcttat gtaatgactg ctgaag                                          26

<210> SEQ ID NO 2
<211> LENGTH: 27
<212> TYPE: DNA
<213> ORGANISM: Artificial Sequence
<220> FEATURE:
<223> OTHER INFORMATION: Synthetic: PCR primer

<400> SEQUENCE: 2
agaaattctt cctacacgaa cagagtc                                         27
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic: PCR primer

<400> SEQUENCE: 3
tgcatccaga gcagttctgc                                                  20

<210> SEQ ID NO 4
<211> LENGTH: 21
<212> TYPE: DNA
<213> ORGANISM: Artificial Sequence
<220> FEATURE:
<223> OTHER INFORMATION: Synthetic: PCR primer

<400> SEQUENCE: 4
cggcgtcatc gtatacacag g                                                21

<210> SEQ ID NO 5
<211> LENGTH: 20
<212> TYPE: DNA
<213> ORGANISM: Artificial Sequence
<220> FEATURE:
<223> OTHER INFORMATION: Synthetic: PCR primer

<400> SEQUENCE: 5
ccaggcttcg tcacagttgc                                                  20

<210> SEQ ID NO 6
<211> LENGTH: 27
<212> TYPE: DNA
<213> ORGANISM: Artificial Sequence
<220> FEATURE:
<223> OTHER INFORMATION: Synthetic: PCR primer

<400> SEQUENCE: 6
cagtgaacta ccgtcaaagt tattacc                                          27

<210> SEQ ID NO 7
<211> LENGTH: 25
<212> TYPE: DNA
<213> ORGANISM: Artificial Sequence
<220> FEATURE:
<223> OTHER INFORMATION: Synthetic: PCR primer

<400> SEQUENCE: 7
gctcttcggc acaagtaata tcaac                                            25

<210> SEQ ID NO 8
<211> LENGTH: 28
<212> TYPE: DNA
<213> ORGANISM: Artificial Sequence
<220> FEATURE:
<223> OTHER INFORMATION: Synthetic: PCR primer

<400> SEQUENCE: 8
tctattttaa attccgtgaa gcaaaacg                                         28

<210> SEQ ID NO 9
<211> LENGTH: 22
<212> TYPE: DNA
<213> ORGANISM: Artificial Sequence
<220> FEATURE:
<223> OTHER INFORMATION: Synthetic: PCR primer
```

<400> SEQUENCE: 9
tggtccatca ggcatcagaa gg                                         22

<210> SEQ ID NO 10
<211> LENGTH: 20
<212> TYPE: DNA
<213> ORGANISM: Artificial Sequence
<220> FEATURE:
<223> OTHER INFORMATION: Synthetic: PCR primer

<400> SEQUENCE: 10
ggcagtgcgg aggtcatttg                                            20

<210> SEQ ID NO 11
<211> LENGTH: 29
<212> TYPE: DNA
<213> ORGANISM: Artificial Sequence
<220> FEATURE:
<223> OTHER INFORMATION: Synthetic: PCR primer

<400> SEQUENCE: 11
tgtctttata ggacatccct gatactttc                                  29

<210> SEQ ID NO 12
<211> LENGTH: 28
<212> TYPE: DNA
<213> ORGANISM: Artificial Sequence
<220> FEATURE:
<223> OTHER INFORMATION: Synthetic: PCR primer

<400> SEQUENCE: 12
tatctactct tgatgccaga aaactagc                                   28

<210> SEQ ID NO 13
<211> LENGTH: 27
<212> TYPE: DNA
<213> ORGANISM: Artificial Sequence
<220> FEATURE:
<223> OTHER INFORMATION: Synthetic: PCR primer

<400> SEQUENCE: 13
aaaattgcaa aatccgttta actaatc                                    27

<210> SEQ ID NO 14
<211> LENGTH: 22
<212> TYPE: DNA
<213> ORGANISM: Artificial Sequence
<220> FEATURE:
<223> OTHER INFORMATION: Synthetic: PCR primer

<400> SEQUENCE: 14
gactgactaa aagaggggaa ag                                         22

<210> SEQ ID NO 15
<211> LENGTH: 22
<212> TYPE: DNA
<213> ORGANISM: Artificial Sequence
<220> FEATURE:
<223> OTHER INFORMATION: Synthetic: PCR primer

<400> SEQUENCE: 15
tcctgaaagc atgaatagta gc                                         22

<210> SEQ ID NO 16

<210> SEQ ID NO 16
<211> LENGTH: 23
<212> TYPE: DNA
<213> ORGANISM: Artificial Sequence
<220> FEATURE:
<223> OTHER INFORMATION: Synthetic: PCR primer

<400> SEQUENCE: 16
ttattaatag cacccggtac aag                                           23

<210> SEQ ID NO 17
<211> LENGTH: 20
<212> TYPE: DNA
<213> ORGANISM: Artificial Sequence
<220> FEATURE:
<223> OTHER INFORMATION: Synthetic: PCR primer

<400> SEQUENCE: 17
ccggcagagg atggttacag                                               20

<210> SEQ ID NO 18
<211> LENGTH: 29
<212> TYPE: DNA
<213> ORGANISM: Artificial Sequence
<220> FEATURE:
<223> OTHER INFORMATION: Synthetic: PCR primer

<400> SEQUENCE: 18
ttgattgata ttccctgaga tatattgtg                                     29

<210> SEQ ID NO 19
<211> LENGTH: 30
<212> TYPE: DNA
<213> ORGANISM: Artificial Sequence
<220> FEATURE:
<223> OTHER INFORMATION: Synthetic: PCR primer

<400> SEQUENCE: 19
ggaagcaata catatcttag aaatgaactc                                    30

<210> SEQ ID NO 20
<211> LENGTH: 22
<212> TYPE: DNA
<213> ORGANISM: Artificial Sequence
<220> FEATURE:
<223> OTHER INFORMATION: Synthetic: PCR primer

<400> SEQUENCE: 20
tcggacaact gcaagcatct ac                                            22

<210> SEQ ID NO 21
<211> LENGTH: 26
<212> TYPE: DNA
<213> ORGANISM: Artificial Sequence
<220> FEATURE:
<223> OTHER INFORMATION: Synthetic: PCR primer

<400> SEQUENCE: 21
gagtgaaaaa gattttgttc aagttg                                        26

<210> SEQ ID NO 22
<211> LENGTH: 20
<212> TYPE: DNA
<213> ORGANISM: Artificial Sequence
<220> FEATURE:
<223> OTHER INFORMATION: Synthetic: PCR primer

<400> SEQUENCE: 22
aaaagtcgct caggttatgc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic: PCR primer

<400> SEQUENCE: 23
agtgcctgaa cctcaatttg                                              20

<210> SEQ ID NO 24
<211> LENGTH: 28
<212> TYPE: DNA
<213> ORGANISM: Artificial Sequence
<220> FEATURE:
<223> OTHER INFORMATION: Synthetic: PCR primer

<400> SEQUENCE: 24
tcgataggat tttcttcaaa atatttac                                     28

<210> SEQ ID NO 25
<211> LENGTH: 26
<212> TYPE: DNA
<213> ORGANISM: Artificial Sequence
<220> FEATURE:
<223> OTHER INFORMATION: Synthetic: PCR primer

<400> SEQUENCE: 25
gtttggtaca gtttatggca tttcac                                       26

<210> SEQ ID NO 26
<211> LENGTH: 29
<212> TYPE: DNA
<213> ORGANISM: Artificial Sequence
<220> FEATURE:
<223> OTHER INFORMATION: Synthetic: PCR primer

<400> SEQUENCE: 26
catggcaata tcaacaatac tcatcttac                                    29

<210> SEQ ID NO 27
<211> LENGTH: 24
<212> TYPE: DNA
<213> ORGANISM: Artificial Sequence
<220> FEATURE:
<223> OTHER INFORMATION: Synthetic: PCR primer

<400> SEQUENCE: 27
caggagcatg aggttcacag tatg                                         24

<210> SEQ ID NO 28
<211> LENGTH: 19
<212> TYPE: DNA
<213> ORGANISM: Artificial Sequence
<220> FEATURE:
<223> OTHER INFORMATION: Synthetic: PCR primer

<400> SEQUENCE: 28
tctctggccc cgcacaatg                                               19

<210> SEQ ID NO 29
<211> LENGTH: 32
<212> TYPE: DNA

```
<213> ORGANISM: Artificial Sequence
<220> FEATURE:
<223> OTHER INFORMATION: Synthetic: PCR primer

<400> SEQUENCE: 29
gggctacaga gatagatatt acagtaactt ag                                    32

<210> SEQ ID NO 30
<211> LENGTH: 20
<212> TYPE: DNA
<213> ORGANISM: Artificial Sequence
<220> FEATURE:
<223> OTHER INFORMATION: Synthetic: PCR primer

<400> SEQUENCE: 30
ccacggctct tccctccaag                                                  20

<210> SEQ ID NO 31
<211> LENGTH: 17
<212> TYPE: DNA
<213> ORGANISM: Artificial Sequence
<220> FEATURE:
<223> OTHER INFORMATION: Synthetic: PCR primer

<400> SEQUENCE: 31
ttccggtcga tcctgcc                                                     17

<210> SEQ ID NO 32
<211> LENGTH: 17
<212> TYPE: DNA
<213> ORGANISM: Artificial Sequence
<220> FEATURE:
<223> OTHER INFORMATION: Synthetic: PCR primer

<400> SEQUENCE: 32
gttgtcctga gccgtcc                                                     17

<210> SEQ ID NO 33
<211> LENGTH: 21
<212> TYPE: DNA
<213> ORGANISM: Artificial Sequence
<220> FEATURE:
<223> OTHER INFORMATION: Synthetic: PCR primer

<400> SEQUENCE: 33
agacgatcca gtttgtatta g                                                21

<210> SEQ ID NO 34
<211> LENGTH: 19
<212> TYPE: DNA
<213> ORGANISM: Artificial Sequence
<220> FEATURE:
<223> OTHER INFORMATION: Synthetic: PCR primer

<400> SEQUENCE: 34
ggcatcctaa ctcacttag                                                   19

<210> SEQ ID NO 35
<211> LENGTH: 19
<212> TYPE: DNA
<213> ORGANISM: Artificial Sequence
<220> FEATURE:
<223> OTHER INFORMATION: Synthetic: PCR primer

<400> SEQUENCE: 35
tctggaaaac aatgtgttc                                                   19
```

<210> SEQ ID NO 36
<211> LENGTH: 19
<212> TYPE: DNA
<213> ORGANISM: Artificial Sequence
<220> FEATURE:
<223> OTHER INFORMATION: Synthetic: PCR primer

<400> SEQUENCE: 36
ggcatgtcga ttctaattc                                              19

<210> SEQ ID NO 37
<211> LENGTH: 36
<212> TYPE: DNA
<213> ORGANISM: Artificial Sequence
<220> FEATURE:
<223> OTHER INFORMATION: Synthetic: PCR primer

<400> SEQUENCE: 37
tccatgatar tcaggcagga cactactcaa ccttcc                           36

<210> SEQ ID NO 38
<211> LENGTH: 29
<212> TYPE: DNA
<213> ORGANISM: Artificial Sequence
<220> FEATURE:
<223> OTHER INFORMATION: Synthetic: PCR primer

<400> SEQUENCE: 38
ttgtcactgt cacagcagaa gccttacgc                                   29

<210> SEQ ID NO 39
<211> LENGTH: 35
<212> TYPE: DNA
<213> ORGANISM: Artificial Sequence
<220> FEATURE:
<223> OTHER INFORMATION: Synthetic: PCR primer

<400> SEQUENCE: 39
agattaacct ctgccgttcc ataatgttgt aacca                            35

<210> SEQ ID NO 40
<211> LENGTH: 30
<212> TYPE: DNA
<213> ORGANISM: Artificial Sequence
<220> FEATURE:
<223> OTHER INFORMATION: Synthetic: PCR primer

<400> SEQUENCE: 40
ccaaacctaa aaccagtaaa ggcgagcagc                                  30

<210> SEQ ID NO 41
<211> LENGTH: 30
<212> TYPE: DNA
<213> ORGANISM: Artificial Sequence
<220> FEATURE:
<223> OTHER INFORMATION: Synthetic: PCR primer

<400> SEQUENCE: 41
tcactcccga cacgccatag aaacgcattt                                  30

<210> SEQ ID NO 42
<211> LENGTH: 33
<212> TYPE: DNA
<213> ORGANISM: Artificial Sequence
<220> FEATURE:

<223> OTHER INFORMATION: Synthetic: PCR primer

<400> SEQUENCE: 42
acaaacagca aaagagcata gcatccgaga act                33

<210> SEQ ID NO 43
<211> LENGTH: 24
<212> TYPE: DNA
<213> ORGANISM: Artificial Sequence
<220> FEATURE:
<223> OTHER INFORMATION: Synthetic: PCR primer

<400> SEQUENCE: 43
caaatatccg tgaaacaaca tgac                24

<210> SEQ ID NO 44
<211> LENGTH: 26
<212> TYPE: DNA
<213> ORGANISM: Artificial Sequence
<220> FEATURE:
<223> OTHER INFORMATION: Synthetic: PCR primer

<400> SEQUENCE: 44
aggattacaa cacaattcac agcagt                26

<210> SEQ ID NO 45
<211> LENGTH: 24
<212> TYPE: DNA
<213> ORGANISM: Artificial Sequence
<220> FEATURE:
<223> OTHER INFORMATION: Synthetic: PCR primer

<400> SEQUENCE: 45
agcaggtttc ccaccggatc acca                24

<210> SEQ ID NO 46
<211> LENGTH: 34
<212> TYPE: DNA
<213> ORGANISM: Artificial Sequence
<220> FEATURE:
<223> OTHER INFORMATION: Synthetic: PCR primer

<400> SEQUENCE: 46
tccgtatatt atcatcaggg catcctttag gcgt                34

<210> SEQ ID NO 47
<211> LENGTH: 25
<212> TYPE: DNA
<213> ORGANISM: Artificial Sequence
<220> FEATURE:
<223> OTHER INFORMATION: Synthetic: PCR primer

<400> SEQUENCE: 47
aagacccaca gttttaccaa gtttt                25

<210> SEQ ID NO 48
<211> LENGTH: 23
<212> TYPE: DNA
<213> ORGANISM: Artificial Sequence
<220> FEATURE:
<223> OTHER INFORMATION: Synthetic: PCR primer

<400> SEQUENCE: 48
aacttggctc ttcttatgtg cgt                23

```
<210> SEQ ID NO 49
<211> LENGTH: 31
<212> TYPE: DNA
<213> ORGANISM: Artificial Sequence
<220> FEATURE:
<223> OTHER INFORMATION: Synthetic: PCR primer

<400> SEQUENCE: 49
cctggataag cgagcgacgt attctctatg c                              31

<210> SEQ ID NO 50
<211> LENGTH: 24
<212> TYPE: DNA
<213> ORGANISM: Artificial Sequence
<220> FEATURE:
<223> OTHER INFORMATION: Synthetic: PCR primer

<400> SEQUENCE: 50
aaaccaaagc cgcccacacc acag                                      24

<210> SEQ ID NO 51
<211> LENGTH: 30
<212> TYPE: DNA
<213> ORGANISM: Artificial Sequence
<220> FEATURE:
<223> OTHER INFORMATION: Synthetic: PCR primer

<400> SEQUENCE: 51
aacctgccaa tccataacca tctgctgctg                                30

<210> SEQ ID NO 52
<211> LENGTH: 21
<212> TYPE: DNA
<213> ORGANISM: Artificial Sequence
<220> FEATURE:
<223> OTHER INFORMATION: Synthetic: PCR primer

<400> SEQUENCE: 52
acgaagccat gcatgcccgc t                                         21

<210> SEQ ID NO 53
<211> LENGTH: 26
<212> TYPE: DNA
<213> ORGANISM: Artificial Sequence
<220> FEATURE:
<223> OTHER INFORMATION: Synthetic: PCR primer

<400> SEQUENCE: 53
acaaaatggc caattcattc aatgaa                                    26

<210> SEQ ID NO 54
<211> LENGTH: 25
<212> TYPE: DNA
<213> ORGANISM: Artificial Sequence
<220> FEATURE:
<223> OTHER INFORMATION: Synthetic: PCR primer

<400> SEQUENCE: 54
cctcctaatc cagaatgtcc tccag                                     25

<210> SEQ ID NO 55
<211> LENGTH: 115
<212> TYPE: DNA
<213> ORGANISM: Escherichia coli

<400> SEQUENCE: 55
```

```
-continued gcgttcttat gtaatgactg ctgaagatgt tgatcttaca ttgaactggg gaaggttgag      60
tagtgtcctg cctgattatc atggacaaga ctctgttcgt gtaggaagaa tttct          115

<210> SEQ ID NO 56
<211> LENGTH: 121
<212> TYPE: DNA
<213> ORGANISM: Escherichia coli

<400> SEQUENCE: 56
tgcatccaga gcagttctgc gttttgtcac tgtcacagca gaagccttac gcttcaggca      60
gatacagaga gaatttcgtc aggcactgtc tgaaactgct cctgtgtata cgatgacgcc     120
g                                                                     121

<210> SEQ ID NO 57
<211> LENGTH: 94
<212> TYPE: DNA
<213> ORGANISM: Escherichia coli

<400> SEQUENCE: 57
ccaggcttcg tcacagttgc aggcctggtt acaacattat ggaacggcag aggttaatct      60
gcagagtggt aataactttg acggtagttc actg                                 94

<210> SEQ ID NO 58
<211> LENGTH: 170
<212> TYPE: DNA
<213> ORGANISM: Salmonella sp.

<400> SEQUENCE: 58
gctcttcggc acaagtaata tcaacggtac agtctctgta gagactttat cgagatcgcc      60
aatcagtcct aacgacgacc cttctttttc ctcaatactg agcggctgct cgcctttgct     120
ggttttaggt ttggcggcgc tacgttttgc ttcacggaat ttaaaataga                 170

<210> SEQ ID NO 59
<211> LENGTH: 257
<212> TYPE: DNA
<213> ORGANISM: Shigella sp.

<400> SEQUENCE: 59
tggtccatca ggcatcagaa ggccttttcg ataatgatac cggcgctctg ctctccctgg      60
gcagggaaat gttccgcctc gaaattctgg aggacattgc ccgggataaa gtcagaactc     120
tccattttgt ggatgagata gaagtctacc tggccttcca gaccatgctc gcagagaaac     180
ttcagctctc cactgccgtg aaggaaatgc gtttctatgg cgtgtcggga gtgacagcaa     240
atgacctccg cactgcc                                                    257

<210> SEQ ID NO 60
<211> LENGTH: 120
<212> TYPE: DNA
<213> ORGANISM: Shigella sp.

<400> SEQUENCE: 60
tgtctttata ggcatcccct gatactttca gaaaattaag accaatacca agttctcgga      60
tgctatgctc ttttgctgtt tgtatatcgt ttgctagttt tctggcatca agagtagata     120

<210> SEQ ID NO 61
<211> LENGTH: 124
<212> TYPE: DNA
<213> ORGANISM: Escherichia coli
```

```
<400> SEQUENCE: 61
aaaattgcaa atccgtttta actaatctca aatatccgtg aaacaacatg acgggaggta      60
acatgaaaaa gctaatgttg gcaattttta tttctgtatt atctttcccc tcttttagtc    120
agtc                                                                 124

<210> SEQ ID NO 62
<211> LENGTH: 76
<212> TYPE: DNA
<213> ORGANISM: Escherichia coli

<400> SEQUENCE: 62
tcctgaaagc atgaatagta gcaattactg ctgtgaattg tgttgtaatc ctgcttgtac     60
cgggtgctat taataa                                                    76

<210> SEQ ID NO 63
<211> LENGTH: 181
<212> TYPE: DNA
<213> ORGANISM: Escherichia coli

<400> SEQUENCE: 63
ccggcagagg atggttacag attagcaggt ttcccaccgg atcaccaagc ttggagagaa     60
gaaccctgga ttcatcatgc accacaaggt tgtggaaatt catcaagaac aattacaggt   120
gatacttgta atgaggagac ccagaatctg agcacaatat atctcaggga atatcaatca   180
a                                                                    181

<210> SEQ ID NO 64
<211> LENGTH: 196
<212> TYPE: DNA
<213> ORGANISM: Escherichia coli

<400> SEQUENCE: 64
ggaagcaata catatcttag aaatgaactc atatttcttg agagaggaat aaatatatca     60
gtaagattgc aaaagaagaa atcaacagta aatccattta tcgcaatcag attaagcagc   120
gatacattaa gacgcctaaa ggatgccctg atgataatat acggaatatc aaaagtagat   180
gcttgcagtt gtccga                                                    196

<210> SEQ ID NO 65
<211> LENGTH: 89
<212> TYPE: DNA
<213> ORGANISM: Campylobacter sp.

<400> SEQUENCE: 65
gagtgaaaaa gattttgttc aagttgcaaa acttggtaaa actgtgggtc ttaagggtta     60
tgtaaaattg cataacctga gcgactttt                                      89

<210> SEQ ID NO 66
<211> LENGTH: 123
<212> TYPE: DNA
<213> ORGANISM: Campylobacter sp.

<400> SEQUENCE: 66
agtgcctgaa cctcaatttg aaggacaaac taaaggaaaa cttggctctt cttatgtgcg     60
tcctatagtt tcaaaagcaa gttttgaata tcttagtaaa tattttgaag aaaatcctat   120
cga                                                                  123
```

```
<210> SEQ ID NO 67
<211> LENGTH: 112
<212> TYPE: DNA
<213> ORGANISM: Yersinia sp.

<400> SEQUENCE: 67
gtttggtaca gtttatggca tttcaccacg cgcctggata agcgagcgac gtattctcta      60
tgctcaccaa ttacttctta attgtaagat gagtattgtt gatattgcca tg            112

<210> SEQ ID NO 68
<211> LENGTH: 79
<212> TYPE: DNA
<213> ORGANISM: Yersinia sp.

<400> SEQUENCE: 68
caggagcatg aggttcacag tatgtgggat ctgttctgtg gtgtgggcgg ctttggttta      60
cattgtgcgg ggccagaga                                                  79

<210> SEQ ID NO 69
<211> LENGTH: 109
<212> TYPE: DNA
<213> ORGANISM: Vibrio cholerae

<400> SEQUENCE: 69
gggctacaga gatagatatt acagtaactt agatattgct ccagcagcag atggttatgg      60
attggcaggt ttccctccgg agcatagagc ttggagggaa gagccgtgg               109

<210> SEQ ID NO 70
<211> LENGTH: 94
<212> TYPE: DNA
<213> ORGANISM: Giardia lamblia virus

<400> SEQUENCE: 70
ttccggtcga tcctgccgga atccgacgct ctccccaagg acacaagcca tgcatgcccg      60
cgcacccggg aggcggcgga cggctcagga caac                                 94

<210> SEQ ID NO 71
<211> LENGTH: 83
<212> TYPE: DNA
<213> ORGANISM: Entamoeba sp.

<400> SEQUENCE: 71
agacgatcca gtttgtatta gtacaaaatg gccaatttat ttaaatgaat tgagaaatga      60
cattctaagt gagttaggat gcc                                             83

<210> SEQ ID NO 72
<211> LENGTH: 247
<212> TYPE: DNA
<213> ORGANISM: Cryptosporidium sp.

<400> SEQUENCE: 72
tctggaaaac aatgtgttca atcagacaca gctcctccta atccagaatg tcctccaggc      60
actatactgg agaatggcac atgtaaatta attcaacaaa ttgataccgt ttgtccttct     120
ggttttgttg aagaaggaaa tagatgtgtt caatatctcc ctgcaaataa aatctgtcct     180
cctggattca atttgtcagg acaacaatgt atggcaccag aatcagctga attagaatcg     240
acatgcc                                                              247
```

```
<210> SEQ ID NO 73
<211> LENGTH: 20
<212> TYPE: DNA
<213> ORGANISM: Oryza sativa

<400> SEQUENCE: 73
ctaatcccag caacccaacc                                              20

<210> SEQ ID NO 74
<211> LENGTH: 30
<212> TYPE: DNA
<213> ORGANISM: Oryza sativa

<400> SEQUENCE: 74
ctaatcaatg tgagacatat gatagaaatc                                   30

<210> SEQ ID NO 75
<211> LENGTH: 19
<212> TYPE: DNA
<213> ORGANISM: Oryza sativa

<400> SEQUENCE: 75
cctgcactgg taagctatg                                               19
```